(12) United States Patent
Liu et al.

(10) Patent No.: US 7,638,548 B2
(45) Date of Patent: Dec. 29, 2009

(54) SPIROINDOLINONE DERIVATIVES

(75) Inventors: Jin-Jun Liu, Warren Township, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 256 days.

(21) Appl. No.: 11/867,155

(22) Filed: Oct. 4, 2007

(65) Prior Publication Data

US 2008/0114013 A1    May 15, 2008

Related U.S. Application Data

(60) Provisional application No. 60/858,039, filed on Nov. 9, 2006.

(51) Int. Cl.
 *A61K 31/404* (2006.01)
 *C07D 209/54* (2006.01)
 *C07D 209/34* (2006.01)
(52) U.S. Cl. ...................... 514/409; 548/407
(58) Field of Classification Search ............... 548/407; 514/409
See application file for complete search history.

(56) References Cited

U.S. PATENT DOCUMENTS 6,573,386 B1 *   6/2003   Gonczi et al. ............... 548/411

FOREIGN PATENT DOCUMENTS

EP    0 947 511 A1   10/1999

OTHER PUBLICATIONS

Hans-Dieter Arndt, pp. 4664-4673, Angewandte Chemie, 2006, 118.

* cited by examiner

*Primary Examiner*—Rebecca L Anderson
*Assistant Examiner*—Jason Nolan
(74) *Attorney, Agent, or Firm*—George W. Johnston; Patricia S. Rocha-Tramaloni

(57) ABSTRACT

There are provided compounds of the general formulas

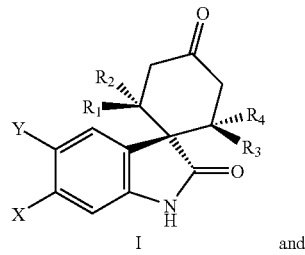

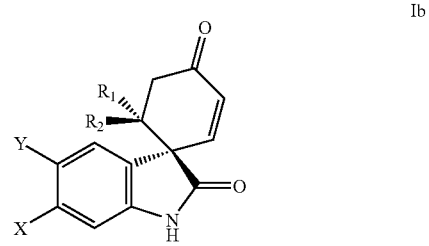

wherein X, Y, $R_1$, $R_2$, $R_3$ and $R_4$ are as described herein. The compounds exhibit anticancer activity.

7 Claims, No Drawings

SPIROINDOLINONE DERIVATIVES

PRIORITY TO RELATED APPLICATION

This Application claims the benefit of U.S. Provisional Application No. 60/858,039, filed, Nov. 9, 2006. which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to spiroindolinone derivatives which act as antagonists of mdm2 interactions and hence are useful as potent and selective anticancer agents. The present compounds are of the general formulas

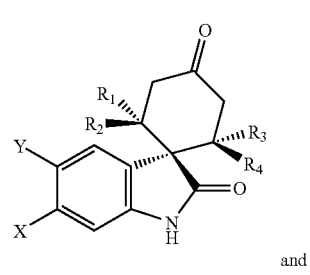

and

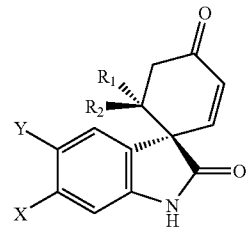

wherein X, Y, $R_1$, $R_2$, $R_3$ and $R_4$ are as described herein and pharmaceutically acceptable salts and esters thereof.

DETAILED DESCRIPTION OF THE INVENTION

There are provided compounds of the formula

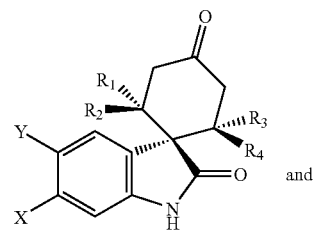

wherein
X is selected from the group consisting of hydrogen, halogen, cyano, nitro, ethynyl, cyclopropyl,
Y is hydrogen,
$R_1$, $R_2$, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_2$ or $R_3/R_4$ is hydrogen and the other not hydrogen and the pharmaceutically acceptable salts and esters thereof.
Preferred are compounds of formula Ia wherein
X is halogen,
Y is hydrogen,
$R_2$ is hydrogen,
$R_4$ is hydrogen and
$R_1$ and $R_3$ are selected from the group consisting of hydrogen, lower alkyl and lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_3$ is a meta-halogen substituted phenyl with or without further substitution.

Further preferred are compounds of formula Ia wherein
X is fluorine, chlorine or bromine,
Y is hydrogen,
$R_2$ is hydrogen,
$R_4$ is hydrogen and
one of $R_1/R_3$ is a meta-halogen substituted phenyl with or without further substitution and the other of $R1/R_3$ is selected from the group consisting of lower alkyl, lower alkenyl, aryl, substituted aryl.

Especially preferred are compounds selected from the group consisting of
Rac-(1R,2S,6S)-6'-chloro-2-(3-chlorophenyl)-6-methoxyspiro[cyclohexane-1,3'-[3H]indole]-2',4(1'H)-dione,
Rac-(1R,2S,6S)-6'-chloro-2-(4-chlorophenyl)-6-methoxyspiro[cyclohexane-1,3'-[3H]indole]-2',4(1'H)-dione,
Rac-(1R,2S,6S)-6'-chloro-2-(3-chloro-2-fluorophenyl)-6-methoxyspiro[cyclohexane-1,3'-[3H]indole]-2',4(1'H)-dione,
Rac-(1R,2S,6S)-6'-chloro-2-(3-cyanophenyl)-6-methoxyspiro[cyclohexane-1,3'-[3H]indole]-2',4(1'H)-dione,
Rac-(1R,2S,6S)-6'-chloro-2-(3-bromophenyl)-6-methoxyspiro[cyclohexane-1,3'-[3H]indole]-2',4(1'H)-dione,
Rac-(1R,2S,6S)-6'-chloro-2-(2-methylphenyl)-6-methoxyspiro[cyclohexane-1,3'-[3H]indole]-2',4(1'H)-dione,
Rac-(1R,2S,6S)-6'-chloro-2-(3,5-dichlorophenyl)-6-methoxyspiro[cyclohexane-1,3'-[3H]indole]-2',4(1'H)-dione,
Rac-(1R,2S,6S)-6'-chloro-2-(3-methylphenyl)-6-methoxyspiro[cyclohexane-1,3'-[3H]indole]-2',4(1'H)-dione,
Rac-(1R,2R,6S)-6'-chloro-2-(3-thienyl)-6-methoxyspiro[cyclohexane-1,3'-[3H]indole]-2',4(1'H)-dione,
Rac-(1R,2S,6R)-6'-chloro-2-(3-chlorophenyl)-6-phenylspiro[cyclohexane-1,3'-[3H]indole]-2',4(1'H)-dione,
Rac-(1S,2S,6R)-6'-chloro-2-(3-chlorophenyl)-6-(5-fluoro-2-methylphenyl)spiro[cyclohexane-1,3'-[3H]indole]-2',4(1'H)-dione,
Rac-(1R,2S,6R)-6'-chloro-2-(3-chlorophenyl)-6-(3-methoxylphenyl)spiro[cyclohexane-1,3'-[3H]indole]-2',4(1'H)-dione,
Rac-(1R,2S,6R)-6'-chloro-2-(3-chlorophenyl)-6-(3-fluorophenyl)spiro[cyclohexane-1,3'-[3H]indole]-2',4(1'H)-dione,
Rac-(1S,2S,6R)-6'-chloro-2-(3-chlorophenyl)-6-(2-methylphenyl)spiro[cyclohexane-1,3'-[3H]indole]-2',4(1'H)-dione,
Rac-(1S,2S,6R)-6'-chloro-2-(3-chlorophenyl)-6-(3-chloro-5-fluorophenyl)spiro[cyclohexane-1,3'-[3H]indole]-2',4(1'H)-dione,
Meso-6'-chloro-2-(3-chlorophenyl)-6-(3-chlorophenyl)spiro[cyclohexane-1,3'-[3H]indole]-2',4(1'H)-dione,
Rac-(1R,2S,6R)-6'-chloro-2-(3-chlorophenyl)-6-(3-methylphenyl)spiro[cyclohexane-1,3'-[3H]indole]-2',4(1'H)-dione,
Rac-(1S,2S,6R)-6'-chloro-2-(3-chlorophenyl)-6-(3-thionyl)spiro[cyclohexane-1,3'-[3H]indole]-2',4(1'H)-dione,
Rac-(1R,2S,6S)-6'-chloro-2-(3-chlorophenyl)-6-ethylspiro[cyclohexane-1,3'-[3H]indole]-2',4(1'H)-dione,
Rac-(1R,2S,6R)-6'-chloro-2-(3-chlorophenyl)-6-ethylspiro[cyclohexane-1,3'-[3H]indole]-2',4(1'H)-dione,
Rac-(1R,2S,6R)-6'-chloro-2-(3-chlorophenyl)-6-vinylspiro[cyclohexane-1,3'-[3H]indole]-2',4(1'H)-dione,
Rac-(1R,2S,6S)-6'-chloro-2-(3-chlorophenyl)-6-vinylspiro[cyclohexane-1,3'-[3H]indole]-2',4(1'H)-dione,
Rac-(1R,2S,6R)-6'-chloro-2-(3-chlorophenyl)-6-isopropylspiro[cyclohexane-1,3'-[3H]indole]-2',4(1'H)-dione,
Rac-(1R,2S,6S)-6'-chloro-2-(3-chlorophenyl)-6-isopropylspiro[cyclohexane-1,3'-[3H]indole]-2',4(1'H)-dione,
Rac-(1R,2S,6R)-6'-chloro-2-(3-chlorophenyl)-6-(1-methylpropyl)-spiro[cyclohexane-1,3'-[3H]indole]-2',4(1'H)-dione,
Rac-(1R,2S,6R)-6'-chloro-2-(3-chlorophenyl)-6-(1-methylpropenyl)spiro[cyclohexane-1,3'-[3H]indole]-2',4(1'H)-dione,
Rac-(1R,2S,6R)-6'-chloro-2-(3-chlorophenyl)-6-iso-propenylspiro[cyclohexane-1,3'-[3H]indole]-2',4(1'H)-dione,
Rac-(1S,2S,6R)-6'-chloro-2-(3-chlorophenyl)-6-(1,1-dimethyl-propyl)spiro[cyclohexane-1,3'-[3H]indole]-2',4(1'H)-dione,
Rac-(1S,2S,6R)-6'-chloro-2-(3-chlorophenyl)-6-(tert-butyl)spiro[cyclohexane-1,3'-[3H]indole]-2',4(1'H)-dione,
Rac-(1R,2S,6R)-6'-chloro-2-(3-chlorophenyl)-6-cyclopentylspiro[cyclohexane-1,3'-[3H]indole]-2',4(1'H)-dione,
Rac-(1R,2S,6S)-6'-chloro-2-(3-chlorophenyl)-6-cyclopentylspiro[cyclohexane-1,3'-[3H]indole]-2',4(1'H)-dione,
Rac-(1R,2S,6R)-6'-chloro-2-(3-chlorophenyl)-6-cyclopropylspiro[cyclohexane-1,3'-[3H]indole]-2',4(1'H)-dione and
Rac-(1R,2S,6S)-6'-chloro-2-(3-chlorophenyl)-6-cyclopropylspiro[cyclohexane-1,3'-[3H]indole]-2',4(1'H)-dione.

In the specification, where indicated, the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkylcarbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the alkyl, aryl, heteroaryl and heterocycle rings are halogen, lower alkoxy, lower alkyl and amino.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

The compounds of formula Ia and Ib as well as their salts that have at least one asymmetric carbon atom may be present as racemic mixtures or different stereoisomers. The various isomers can be isolated by known separation methods, e.g., chromatography.

Compounds disclosed herein and covered by formula Ia and Ib above may exhibit tautomerism or structural isomerism. It is intended that the invention encompasses any tautomeric or structural isomeric form of these compounds, or mixtures of such forms, and is not limited to any one tautomeric or structural isomeric form depicted in formula Ia and Ib above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

The present invention provides methods for the synthesis of spiroindolinones. The compounds of the invention can be prepared by processes known in the art. Suitable processes for synthesizing these compounds are provided in the examples. Generally, the compounds of the invention can be prepared according to the synthesis schemes provided below.

The following synthetic schemes provide two general methods for preparation of compounds of the invention, i.e., compounds of formula Ia. In method A, illustrated in scheme 1, an indolone of formula IV is converted to a compound of formula Ia and Ib through a Diels-Alder reaction with silyl enol ether V followed by treatment of the intermediates VIa and VIb with base.

Scheme 1

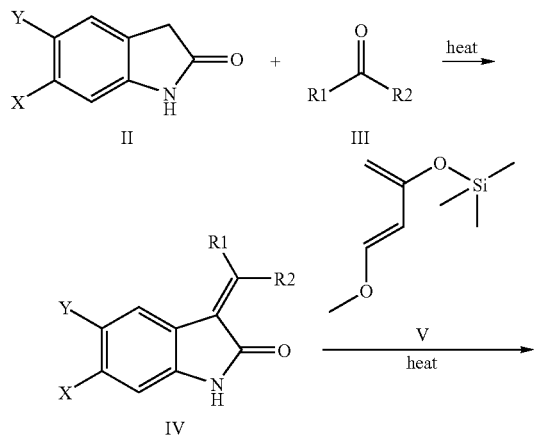

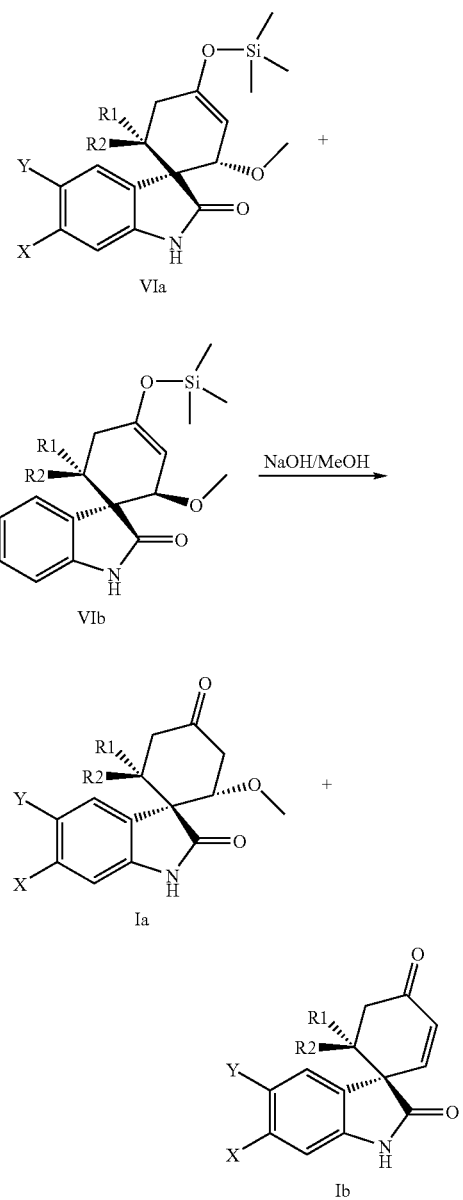

In method B, shown in scheme 2, a compound of formula Ib is converted to a compound of formula Ia by a 1,4-addition reaction with Grignard reagent.

Scheme 2

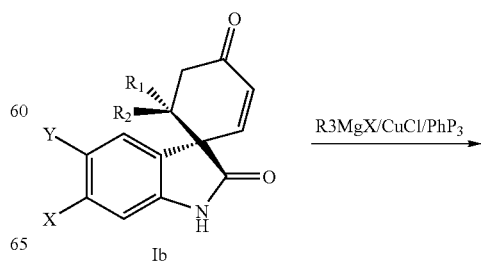

-continued

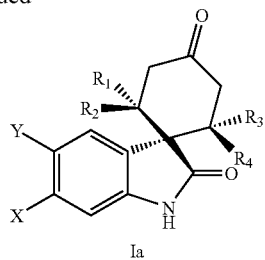

Ia

A compound of formula Ia is converted to a compound of formula Ib by heating with microwave in the presence of acid catalyst (Scheme 3)

Scheme 3

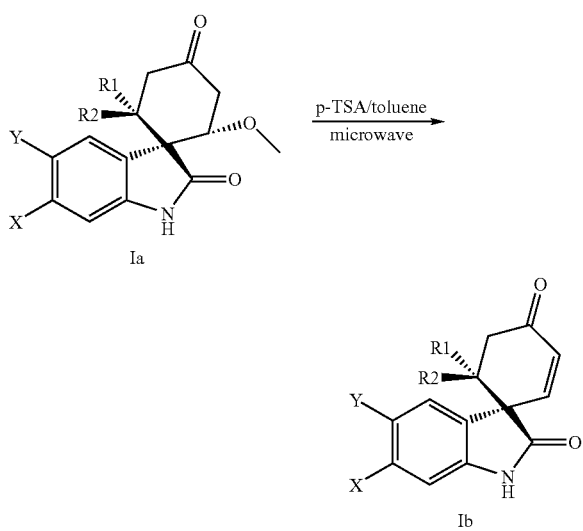

The following examples and references are provided to aid the understanding of the present invention, the true scope of which is set forth in the appended claims.

EXAMPLE 1

Preparation of intermediate E/Z-6-chloro-3-[1-(3-chlorophenyl)-methylidene]-1,3-dihydro-indol-2-one

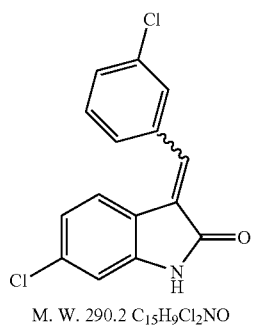

M. W. 290.2 $C_{15}H_9Cl_2NO$

To the mixture of 6-chlorooxindole (16.2 g, 92 mmol) (Crescent) and 3-chloro-benzaldehyde (12.9 g, 92 mmol) (Aldrich) in methanol (109 mL) was added pyrrolidine (6.55 g, 92 mmol) (Aldrich) dropwise. The mixture was then heated at 70° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 25.2 g, 94.4%).

EXAMPLE 2

Preparation of intermediate E/Z-6-chloro-3-[1-(4-chlorophenyl)-methylidene]-1,3-dihydro-indol-2-one

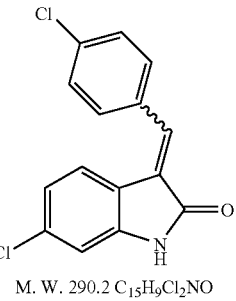

M. W. 290.2 $C_{15}H_9Cl_2NO$

In a manner similar to the method described in example 1, 6-chlorooxindole (5.1 g, 29.8 mmol) (Avocado) was reacted with 4-chloro-benzaldehyde (4.3 g, 29.8 mmol) (Aldrich) in isopropanol to give a mixture of E/Z-6-chloro-3-(4-chloro-benzylidene)-1,3-dihydro-indol-2-one as a bright yellow solid (Yield 7.4 g, 85.4%) and used for the next step without further purification.

EXAMPLE 3

Preparation of intermediate E/Z-6-chloro-3-[1-(3-chloro-2-fluorophenyl)-methylidene]-1,3-dihydro-indol-2-one

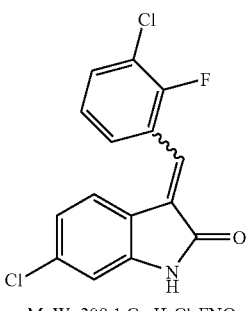

M. W. 308.1 $C_{15}H_8Cl_2FNO$

In a manner similar to the method described in example 1, 6-chlorooxindole (5.20 g, 31.2 mmol) (Crescent) and 3-chloro-4-fluoro-benzaldehyde (5.0 g, 31.2 mmol) (Aldrich) in isopropanol to give a mixture of E/Z-6-chloro-3-(3-chloro-4-fluoro-benzylidene)-1,3-dihydro-indol-2-one as a bright yellow solid (Yield 8.89 g, 92.5%) and used for the next step without further purification.

EXAMPLE 4

Preparation of Intermediate E/Z-6-chloro-3-[1-(3-fluoro-6-methylphenyl)-methylidene]-1,3-dihydro-indol-2-one

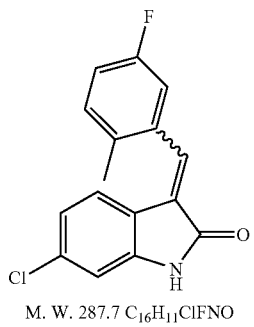

M. W. 287.7 $C_{16}H_{11}ClFNO$

In a manner similar to the method described in example 1, 6-chlorooxindole (4.17 g, 25 mmol) (Avocado) and 3-fluoro-6-methyl-benzaldehyde (3.45 g, 25 mmol) (Aldrich) in isopropanol to give a mixture of E/Z-6-chloro-3-(3-fluoro-6-methyl-benzylidene)-1,3-dihydro-indol-2-one as a yellow solid (Yield 6.44 g, 89.8%) and used for the next step without further purification.

EXAMPLE 5

Preparation of intermediate E/Z-6-chloro-3-[1-(3,5-difluorophenyl)-methylidene]-1,3-dihydro-indol-2-one

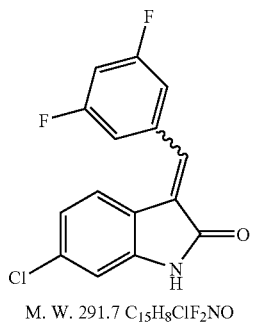

M. W. 291.7 $C_{15}H_8ClF_2NO$

In a manner similar to the method described in example 1, 6-chlorooxindole (1.05 g, 6.27 mmol) (Avocado) and 3,5-difluoro-benzaldehyde (0.89 g, 6.27 mmol) (Aldrich) in isopropanol to give a mixture of E/Z-6-chloro-3-(3,5-difluoro-benzylidene)-1,3-dihydro-indol-2-one as a bright yellow solid (Yield 1.2 g, 66.7%) and used for the next step without further purification.

EXAMPLE 6

Preparation of intermediate E/Z-6-chloro-3-[1-(3-cyano-phenyl)-methylidene]-1,3-dihydro-indol-2-one

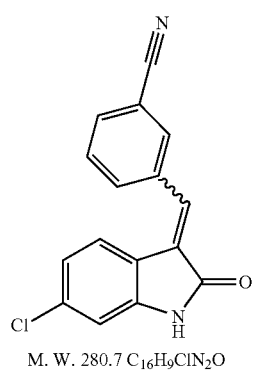

M. W. 280.7 $C_{16}H_9ClN_2O$

In a manner similar to the method described in example 1, 6-chlorooxindole (4.12 g, 24.7 mmol) (Avocado) and 3-cyano-benzaldehyde (3.3 g, 24.7 mmol) (Aldrich) in isopropanol to give a mixture of E/Z-E/Z-6-chloro-3-(3-cyano-benzylidene)-1,3-dihydro-indol-2-one as a bright yellow solid (Yield 5.4 g, 77.9%) and used for the next step without further purification.

EXAMPLE 7

Preparation of intermediate E/Z-6-chloro-3-[1-(3-bromophenyl)-methylidene]-1,3-dihydro-indol-2-one

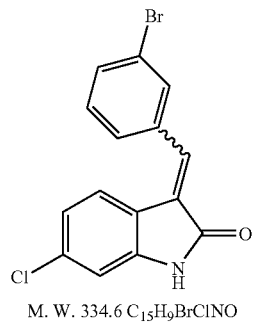

M. W. 334.6 $C_{15}H_9BrClNO$

In a manner similar to the method described in example 1, 6-chlorooxindole (4.12 g, 24.7 mmol) (Avocado) and 3-bromo-benzaldehyde (4.64 g, 24.7 mmol) (Aldrich) in isopropanol to give a mixture of E/Z-E/Z-6-chloro-3-(3-bromo-benzylidene)-1,3-dihydro-indol-2-one as a bright yellow solid (Yield 7.7 g, 93.9%) and used for the next step without further purification.

EXAMPLE 8

Preparation of intermediate E/Z-6-chloro-3-(1-pyridin-2-yl-methylidene)-1,3-dihydro-indol-2-one

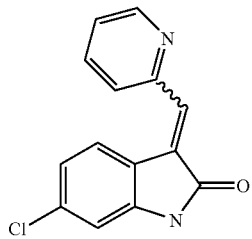

M. W. 256.7 C$_{14}$H$_9$ClN$_2$O

In a manner similar to the method described in example 1, 6-chlorooxindole (4.12 g, 24.7 mmol) (Avocado) and pyridine-2-carbaldehyde (2.96 g, 24.7 mmol) (Aldrich) in isopropanol to give a mixture of E/Z-6-chloro-3-pyridi-2-yl-methene-1,3-dihydro-indol-2-one as a bright yellow solid (Yield 6.0 g, 94.6%) and used for the next step without further purification.

EXAMPLE 9

Preparation of Intermediate E/Z-6-chloro-3-[1-(3-methoxyphenyl)-methylidene]-1,3-dihydro-indol-2-one

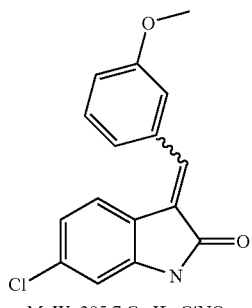

M. W. 285.7 C$_{16}$H$_{12}$ClNO$_2$

In a manner similar to the method described in example 1, 6-chlorooxindole (4.12 g, 24.7 mmol) (Apollo) and 3-methoxy-benzaldehyde (3.36 g, 24.7 mmol) (Avocado) in isopropanol to give a mixture of E/Z-E/Z-6-chloro-3-(3-methoxy-benzylidene)-1,3-dihydro-indol-2-one as a bright yellow solid (Yield 4.9 g, 69.4%) and used for the next step without further purification.

EXAMPLE 10

Preparation of intermediate E/Z-6-chloro-3-[1-(3-fluorophenyl)-methylidene]-1,3-dihydro-indol-2-one

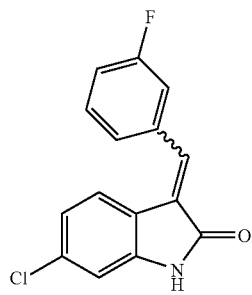

M. W. 273.7 C$_{15}$H$_9$ClFNO

In a manner similar to the method described in example 1, 6-chlorooxindole (4.12 g, 24.7 mmol) (Avocado) and 3-fluoro-benzaldehyde (3.0 g, 24.7 mmol) (Aldrich) in isopropanol to give a mixture of E/Z-E/Z-6-chloro-3-(3-fluoro-benzylidene)-1,3-dihydro-indol-2-one as a yellow solid (Yield 5.7 g, 85.1%). and used for the next step without further purification.

EXAMPLE 11

Preparation of intermediate E/Z-6-chloro-3-[1-(2-methylphenyl)-methylidene]-1,3-dihydro-indol-2-one

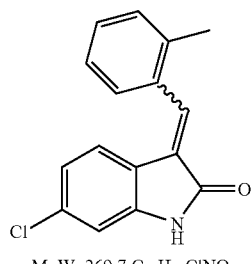

M. W. 269.7 C$_{16}$H$_{12}$ClNO

In a manner similar to the method described in example 1, 6-chlorooxindole (4.12 g, 24.7 mmol) (Avocado) and 2-methyl-benzaldehyde (2.96 g, 24.7 mmol) (Avocado) in isopropanol to give a mixture of E/Z-E/Z-6-chloro-3-(2-methyl-benzylidene)-1,3-dihydro-indol-2-one as a bright yellow solid (Yield 5.7 g, 85.6%) and used for the next step without further purification.

EXAMPLE 12

Preparation of intermediate E/Z-6-chloro-3-[1-(3-trifluromethylphenyl)-methylidene]-1,3-dihydro-indol-2-one

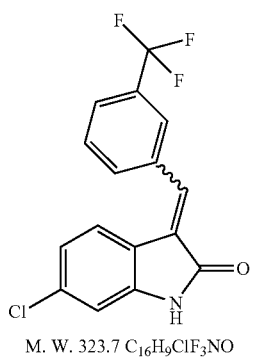

M. W. 323.7 $C_{16}H_9ClF_3NO$

In a manner similar to the method described in example 1, 6-chlorooxindole (4.12 g, 24.7 mmol) (Crescent) and 3-trifluoromethyl-benzaldehyde (3.4 mL, 24.7 mmol) (Aldrich) in isopropanol to give a mixture of E/Z-6-chloro-3-(3-trifluoromethyl-benzylidene)-1,3-dihydro-indol-2-one as a bright yellow solid (Yield 6.13 g, 76.7%) and used for the next step without further purification.

EXAMPLE 13

Preparation of intermediate E/Z-6-chloro-3(2-methyl-allylidene)-1,3-dihydro-indol-2-one

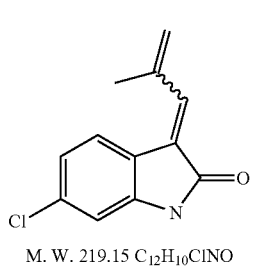

M. W. 219.15 $C_{12}H_{10}ClNO$

In a manner similar to the method described in example 1, 6-chlorooxindole (2.06 g, 12.3 mmol) (Apollo) and 2-methyl-propenal (1.32 g, 12.3 mmol) (Aldrich) in isopropanol to give a mixture of E/Z-6-chloro-3(2-methyl-allylidene)-1,3-dihydro-indol-2-one as a yellow solid (Yield 0.16 g, 5.9%) and used for the next step without further purification.

EXAMPLE 14

Preparation of intermediate E/Z-6-chloro-3-[1-(3,5-dichlorophenyl)-methylidene]-1,3-dihydro-indol-2-one

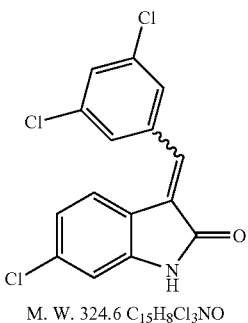

M. W. 324.6 $C_{15}H_8Cl_3NO$

In a manner similar to the method described in example 1, 6-chlorooxindole (2.06 g, 12.3 mmol) (Avocado) and 3,5-dichloro-benzaldehyde (2.2 g, 12.3 mmol) (Aldrich) in isopropanol to give a mixture of E/Z-6-chloro-3-[1-(3,5-dichlorophenyl)-methylidene]-1,3-dihydro-indol-2-one as a bright yellow solid (Yield 3.0 g, 75.2%) and used for the next step without further purification.

EXAMPLE 15

Preparation of Intermediate E/Z-6-chloro-3 E/Z-6-chloro-3-[1-(3-methylphenyl)-methylidene]-1,3-dihydro-indol-2-one

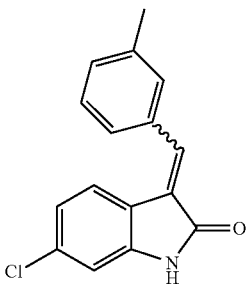

M. W. 269.7 $C_{16}H_{12}ClNO$

In a manner similar to the method described in example 1, 6-chlorooxindole (4.12 g, 24.7 mmol) (Avocado) and 3-methyl-benzaldehyde (2.96 g, 24.7 mmol) (Aldrich) in isopropanol to give a mixture of E/Z-6-chloro-3-[1-(3-methylphenyl)-methylidene]-1,3-dihydro-indol-2-one as a bright yellow solid (Yield 5.4 g, 73.3%) and used for the next step without further purification.

EXAMPLE 16

Preparation of intermediate E/Z-6-chloro-3-(1-pyridi-3-ylmethylidene)-1,3-dihydro-indol-2-one

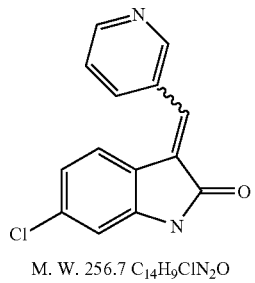

M. W. 256.7 C$_{14}$H$_9$ClN$_2$O

In a manner similar to the method described in example 1, 6-chlorooxindole (2.06 g, 12.3 mmol) (Apollo) and pyridine-3-carbaldehyde (1.31 g, 12.3 mmol) (Aldrich) in isopropanol to give a mixture of E/Z-6-chloro-3-(1-pyridi-3-ylmethylidene)-1,3-dihydro-indol-2-one as a bright yellow solid (Yield 2.4 g, 75.9%) and used for the next step without further purification.

EXAMPLE 17

Preparation of intermediate E/Z-6-chloro-3-(1-thiophen-3-yl-methylidene)-1,3-dihydro-indol-2-one

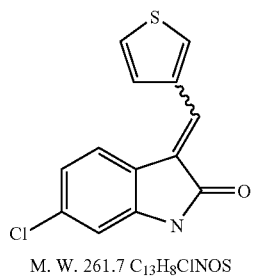

M. W. 261.7 C$_{13}$H$_8$ClNOS

In a manner similar to the method described in example 1, 6-chlorooxindole (2.06 g, 12.3 mmol) (Apollo) and thiophenyl carbaldehyde (1.38 g, 12.3 mmol) (Aldrich) in isopropanol to give a mixture of E/Z-6-chloro-3-(1-thiophen-3-yl-methylidene)-1,3-dihydro-indol-2-one as a bright yellow solid (Yield 2.7 g, 83.9%) and used for the next step without further purification.

EXAMPLE 18

Preparation of Rac-(1R,2R)-6'-chloro-2-(3-chlorophenyl)spiro[5-cyclohexene-1,3'-[3H]indole]-2',4 (1'H)-dione, Rac-(1R,2S)-6'-chloro-2-(3-chlorophenyl)spiro[5-cyclohexene-1,3'-[3H]indole]-2',4(1'H)-dione, and Rac-(1R,2S,6S)-6'-chloro-2-(3-chlorophenyl)-6-methoxyspiro[cyclohexane-1,3'-[3H]indole]-2',4(1'H)-dione (Scheme 1)

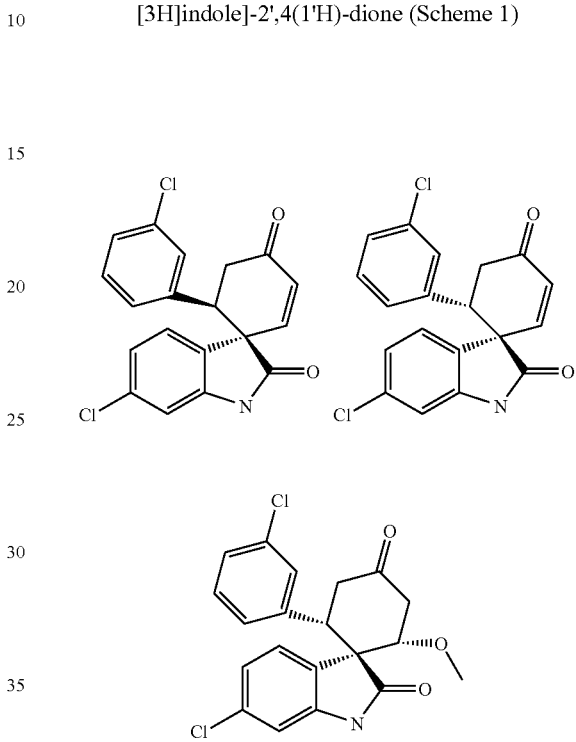

To a suspension of E/Z-6-chloro-3-(3-chloro-benzylidene)-1,3-dihydro-indol-2-one (5.43 g, 15.0 mmol) in toluene (50 mL) in a sealed tube was added (3-methoxy-1-methylene-allyloxy)-trimethyl-silane (3.44 g, 20.0 mmol). The reaction mixture was allowed to stir at 140° C. for 24 hrs. The solvent was removed by concentration. The residue was dissolved in MeOH (50 mL) and treated with 4 N NaOH (5 mL) at rt for 2 hrs. The reaction mixture was then diluted with AcOEt and washed with water and brine. After concentration the residue was purified by flash column (5% -30% AcOEt in Hex) to give rac-(1R,2R)-6'-chloro-2-(3-chlorophenyl)spiro [5-cyclohexene-1,3'-[3H]indole]-2',4(1'H)-dione (0.46 g, 18.6%) as white amorphous. HRMS (ES$^+$) m/z Calcd for C$_{19}$H$_{13}$ClN$_2$O$_2$+H [(M+H)$^+$]: 358.0396. Found: 358.0395; rac-(1R,2S)-6'-chloro-2-(3-chlorophenyl)spiro[5-cyclohexene-1,3'-[3H]indole]-2',4(1'H)-dione (1.11 g 20.7%) as white amorphous. HRMS (ES$^+$) m/z Calcd for C$_{19}$H$_{13}$ClN$_2$O$_2$+H [(M+H)$^+$]: 358.0396. Found: 358.0394; and rac-(1R,2S,6S)-6'-chloro-2-(3-chlorophenyl)-6-methoxyspiro[cyclohexane-1,3'-[3H]indole]-2',4(1'H)-dione (2.33 g, 39.8%) as white amorphous. HRMS (ES$^+$) m/z Calcd for C$_{20}$H$_{17}$ClN$_3$O$_2$+H [(M+H)$^+$]: 390.0658. Found: 390.0656.

EXAMPLE 19

Preparation of Rac-(1R,2R)-6'-chloro-2-(4-chlorophenyl)spiro[5-cyclohexane-1,3'-[3H]indole]-2',4(1'H)-dione, Rac-(1R,2S)-6'-chloro-2-(4-chlorophenyl)spiro[5-cyclohexene-1,3'-[3H]indole]-2'4(1'H)-dione, and Rac-(1R,2S,6S)-6'-chloro-2-(4-chlorophenyl)-6-methoxyspiro[cyclohexane-1,3'-[3H]indole]-2',4(1'H)-dione

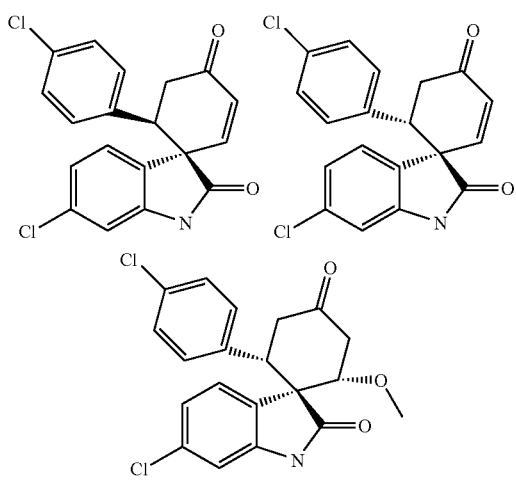

In a manner similar to the method described in example 16, E/Z-6-chloro-3-(4-chloro-benzylidene)-1,3-dihydro-indol-2-one (0.36 g, 1.0 mmol) was reacted with (3-methoxy-1-methylene-allyloxy)-trimethyl-silane (0.19 g, 1.0 mmol) in toluene to give rac-(1R,2R)-6'-chloro-2-(4-chlorophenyl)spiro[5-cyclohexene-1,3'-[3H]indole]-2',4(1'H)-dione (0.03 g, 8.6%) as white amorphous. HRMS (ES$^+$) m/z Calcd for $C_{19}H_{13}ClN_2O_2$+H [(M+H)$^+$]: 358.0396. Found: 358.0395; rac-(1R,2S )-6'-chloro-2-(4-chlorophenyl)spiro[5-cyclohexene-1,3'-[3H]indole]-2',4(1'H)-dione (0.09 g 23.0%) as white amorphous. HRMS (ES$^+$) m/z Calcd for $C_{19}H_{13}ClN_2O_2$+H [(M+H)$^+$]: 358.0396. Found: 358.0395; and rac-(1R,2S,6S)-6'-chloro-2-(4-chlorophenyl)-6-methoxyspiro[cyclohexane-1,3'-[3H]indole]-2',4(1'H)-dione (0.15 g, 37.2%) as white amorphous. HRMS (ES$^+$) m/z Calcd for $C_{20}H_{17}ClN_3O_2$+H [(M+H)$^+$]: 390.0658. Found: 390.0654.

EXAMPLE 20

Preparation of Rac-(1R,2R)-6'-chloro-2-(3-chloro-2-fluorophenyl)spiro[5-cyclohexene-1,3'-[3H]indole]-2',4(1'H)-dione, Rac-(1R,2S)-6'-chloro-2-(3-chloro-2-fluorophenyl)spiro[5-cyclohexane-1,3'-[3H]indole]-2',4(1'H)-dione, and Rac-(1R,2S,6S)-6'-chloro-2-(3-chloro-2-fluorophenyl)-6-methoxyspiro[cyclohexane-1,3'-[3H]indole]-2',4(1'H)-dione

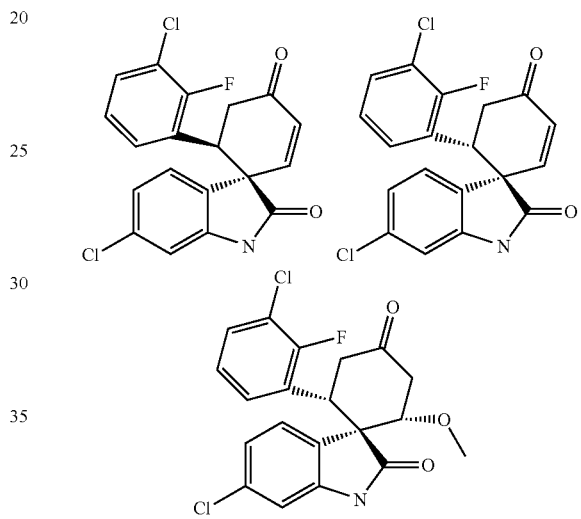

In a manner similar to the method described in example 16, E/Z-6-chloro-3-(3-chloro-2-fluorobenzylidene)-1,3-dihydro-indol-2-one (1.90 g 5.0 mmol) was reacted with (3-methoxy-1-methylene-allyloxy)-trimethyl-silane (0.95 g, 5.0 mmol) in toluene to give rac-(1R,2R)-6'-chloro-2-(3-chloro-2-fluorophenyl)spiro[5-cyclohexene-1,3'-[3H]indole]-2',4(1'H)-dione (0.15 g 4.2%) as white amorphous. HRMS (ES$^+$) m/z Calcd for $C_{19}H_{12}FCl_2NO_2$+H [(M+H)$^+$]: 376.0302. Found: 376.0299; rac-(1R,2S)-6'-chloro-2-(3-chloro-2-fluorophenyl)spiro[5-cyclohexene-1,3'-[3H]indole]-2',4(1'H)-dione (1.02 g 28.5%) as white amorphous. HRMS (ES$^+$) m/z Calcd for $C_{19}H_{12}FCl_2NO_2$+H [(M+H)$^+$]: 376.0302. Found: 376.0304; and rac-(1R,2S,6S)-6'-chloro-2-(3-chloro-2-fluorophenyl)-6-methoxyspiro[cyclohexane-1,3'-[3H]indole]-2',4(1'H)-dione (1.65 g 42.3%) as white amorphous. HRMS (ES$^+$) m/z Calcd for $C_{20}H_{16}FCl_2NO_3$+H [(M+H)$^+$]: 408.0564. Found: 408.0561.

EXAMPLE 21

Preparation of Rac-(1R,2R)-6'-chloro-2-(3-cyanophenyl)spiro[5-cyclohexene-1,3'-[3H]indole]-2',4(1'H)-dione, Rac-(1R,2S)-6'-chloro-2-(3-cyanophenyl)spiro[5-cyclohexene-1,3'-[3H]indole]-2',4(1'H)-dione, and Rac-(1R,2S,6S)-6'-chloro-2-(3-cyanophenyl)-6-methoxyspiro[cyclohexane-1,3'-[3H]indole]-2',4(1'H)-dione

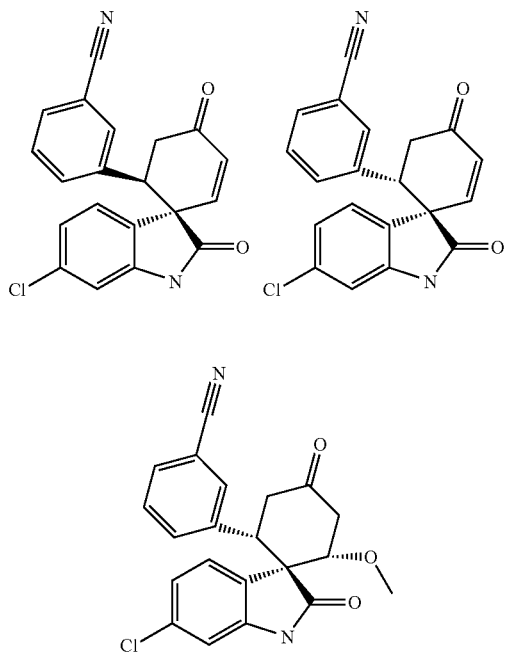

In a manner similar to the method described in example 16, E/Z-6-chloro-3-(3-cyanobenzylidene)-1,3-dihydro-indol-2-one (0.28 g, 1.0 mmol) was reacted with (3-methoxy-1-methylene-allyloxy)-trimethyl-silane (0.21 g, 1.2 mmol) in toluene to give rac-(1R,2R)-6'-chloro-2-(3-cyanophenyl)spiro[5-cyclohexene-1,3'-[3H]indole]-2',4(1'H)-dione (0.02 g, 5.7%) as white amorphous. HRMS (ES$^+$) m/z Calcd for $C_{20}H_{13}ClN_2O_2$+H [(M+H)$^+$]: 349.0739. Found: 349.0736; rac-(1R,2S)-6'-chloro-2-(3-cyanophenyl)spiro[5-cyclohexene-1,3'-[3H]indole]-2',4(1'H)-dione (0.10 g 28.6%) as white solid. HRMS (ES$^+$) m/z Calcd for $C_{20}H_{13}ClN_2O_2$+H [(M+H)$^+$]: 349.0739. Found: 349.0738; and rac-(1R,2S,6S)-6'-chloro-2-(3-cyanophenyl)-6-methoxyspiro[cyclohexane-1,3'-[3H]indole]-2',4(1'H)-dione (0.17 g, 44.7%) as white solid. HRMS (ES$^+$) m/z Calcd for $C_{21}H_{17}ClN_2O_3$+H [(M+H)$^+$]: 381.1001. Found: 381.1000.

EXAMPLE 22

Preparation of Rac-(1R,2R)-6'-chloro-2-(3-bromophenyl)spiro[5-cyclohexene-1,3'-[3H]indole]-2',4(1'H)-dione, Rac-(1R,2S)-6'-chloro-2-(3-bromophenyl)spiro[5-cyclohexene-1,3'-[3H]indole]-2',4(1'H)-dione, and Rac-(1R,2S,6S)-6'-chloro-2-(3-bromophenyl)-6-methoxyspiro[cyclohexane-1,3'-[3H]indole]-2',4(1'H)-dione

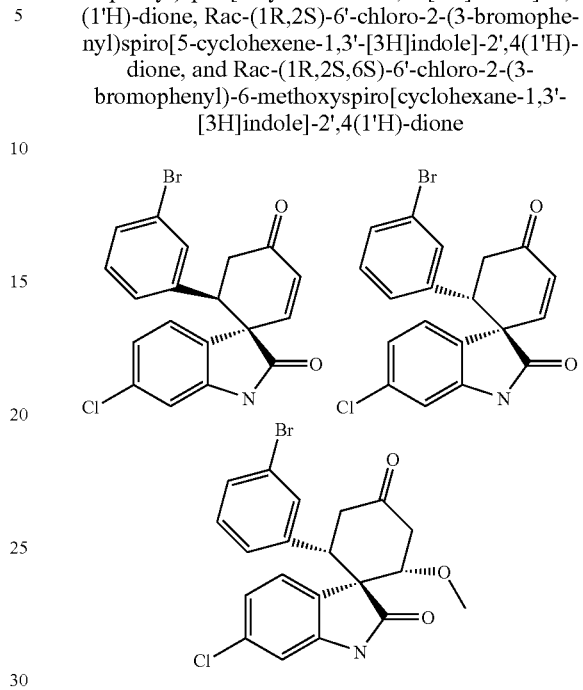

In a manner similar to the method described in example 16, E/Z-6-chloro-3-(3-bromobenzylidene)-1,3-dihydro-indol-2-one (0.33 g, 1.0 mmol) was reacted with (3-methoxy-1-methylene-allyloxy)-trimethyl-silane (0.21 g, 1.2 mmol) in toluene to give rac-(1R,2R)-6'-chloro-2-(3-bromophenyl)spiro[5-cyclohexene-1,3'-[3H]indole]-2',4(1'H)-dione (0.02 g, 5.0%) as white amorphous. HRMS (ES$^+$) m/z Calcd for $C_{19}H_{13}BrClNO_2$+H [(M+H)$^+$]: 401.9891. Found: 401.9889; rac-(1R,2S)-6'-chloro-2-(3-bromophenyl)spiro[5-cyclohexene-1,3'-[3H]indole]-2',4(1'H)-dione (0.11 g 27.5%) as white solid. HRMS (ES$^+$) m/z Calcd for $C_{19}H_{13}BrClNO_2$+H [(M+H)$^+$]: 401.9891. Found: 401.9888; and rac-(1R,2S,6S)-6'-chloro-2-(3-bromophenyl)-6-methoxyspiro[cyclohexane-1,3'-[3H]indole]-2',4(1'H)-dione (0.15 g, 34.9%) as white solid. HRMS (ES$^+$) m/z Calcd for $C_{20}H_{17}BrClNO_3$+H [(M+H)$^+$]: 434.0153. Found: 434.0152.

EXAMPLE 23

Preparation of Rac-(1R,2R)-6'-chloro-2-(2-pyridinyl)spiro[5-cyclohexene-1,3'-[3H]indole]-2',4(1'H)-dione

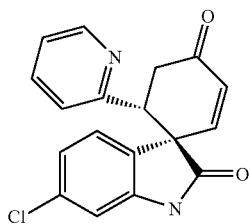

In a manner similar to the method described in example 16, E/Z-6-chloro-3-(pyridine-2-yl)-1,3-dihydro-indol-2-one (0.257 g, 1.0 mmol) was reacted with (3-methoxy-1-methylene-allyloxy)-trimethyl-silane (0.21 g, 1.2 mmol) in toluene to give rac-(1R,2R)-6'-chloro-2-(pyridin-2-yl)spiro[5-cyclohexene-1,3'-[3H]indole]-2',4(1'H)-dione (0.013 g, 3.9%) as white amorphous. HRMS (ES+) m/z Calcd for $C_{18}H_{13}ClN_2O_2$+H [(M+H)+]: 325.0739. Found: 325.0736.

EXAMPLE 24

Preparation of Rac-(1R,2R)-6'-chloro-2-(3-methoxyphenyl)spiro[5-cyclohexene-1,3'-[3H]indole]-2',4(1'H)-dione, and Rac-(1R,2S)-6'-chloro-2-(3-methoxyphenyl)spiro[5-cyclohexene-1,3'-[3H]indole]-2',4(1'H)-dione

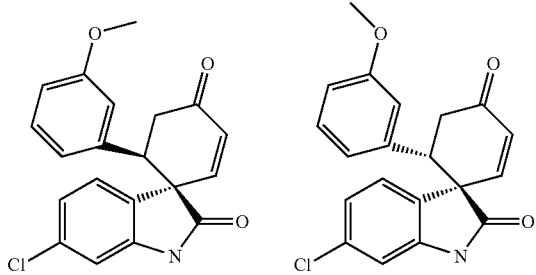

In a manner similar to the method described in example 16, E/Z-6-chloro-3-(3-methoxbenzylidene)-1,3-dihydro-indol-2-one (0.29 g, 1.0 mmol) was reacted with (3-methoxy-1-methylene-allyloxy)-trimethyl-silane (0.21 g, 1.2 mmol) in toluene at 140° C. for 60 hrs. to give rac-(1R,2R)-6'-chloro-2-(3-methoxyphenyl)spiro[5-cyclohexene-1,3'-[3H]indole]-2',4(1'H)-dione (0.020 g, 5.6%) as white amorphous. HRMS (ES+) m/z Calcd for $C_{20}H_{16}ClNO_3$+H [(M+H)+]: 354.0892. Found: 354.0891; rac-(1R,2S)-6'-chloro-2-(3-methoxyphenyl)spiro[5-cyclohexene-1,3'-[3H]indole]-2',4(1'H)-dione (0.086 g 24.2%) as white amorphous. HRMS (ES+) m/z Calcd for $C_{20}H_{16}ClNO_3$+H [(M+H)+]: 354.0892. Found: 354.0889.

EXAMPLE 25

Preparation of Rac-(1R,2S)-6'-chloro-2-(3-fluorophenyl)spiro[5-cyclohexene-1,3'-[3H]indole]-2',4(1'H)-dione

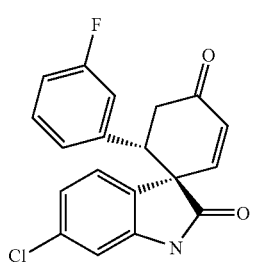

To a suspension of E/Z-6-chloro-3-(3-fluorophenyl)-1,3-dihydro-indol-2-one (0.27 g, 1.0 mmol) in toluene (50 mL) in a sealed tube was added reagent (3-methoxy-1-methylene-allyloxy)-trimethyl-silane (0.21 g, 1.2 mmol) and the reaction mixture was allowed to stir at 140° C. for 24 hrs. The solution was cooled to rt and the tube was opened, and a catalytic amount of p-TSA was added. The reaction mixture was refluxed overnight. After solvent evaporation, the residue was dissolved in CH2Cl2 (100 mL) and washed with sat. NaHCO3 (20 mL), and brine and dried. After concentration the residue was purified by flash column (5%-40% AcOEt in Hex) to give rac-(1R,2R)-6'-chloro-2-(3-fluorophenyl)spiro[5-cyclohexene-1,3'-[3H]indole]-2',4(1'H)-dione (0.17 g, 50.0%) as white amorphous. HRMS (ES+) m/z Calcd for $C_{19}H_{13}ClFNO_2$+H [(M+H)+]: 342.0692. Found: 342.0691.

EXAMPLE 26

Preparation of Rac-(1R,2S)-6'-chloro-2-(2-methylphenyl)spiro[5-cyclohexene-1,3'-[3H]indole]-2',4(1'H)-dione, and Rac-(1R,2S,6S)-6'-chloro-2-(2-methylphenyl)-6-methoxyspiro[cyclohexane-1,3'-[3H]indole]-2',4(1'H)-dione

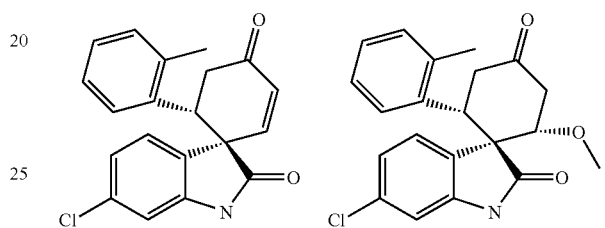

In a manner similar to the method described in example 16, E/Z-6-chloro-3-(2-methylbenzylidene)-1,3-dihydro-indol-2-one (0.27 g, 1.0 mmol) was reacted with (3-methoxy-1-methylene-allyloxy)-trimethyl-silane (0.21 g, 1.2 mmol) in toluene to give rac-(1R,2S)-6'-chloro-2-(2-methylphenyl)spiro[5-cyclohexene-1,3'-[3H]indole]-2',4(1'H)-dione (0.016 g, 4.6%) as white solid. HRMS (ES+) m/z Calcd for $C_{20}H_{16}ClNO_2$+H [(M+H)+]: 338.0943. Found: 338.0941; and rac-(1R,2S,6S)-6'-chloro-2-(2-methylphenyl)-6-methoxyspiro[cyclohexane-1,3'-[3H]indole]-2',4(1'H)-dione (0.038 g, 10.2%) as white amorphous. HEMS (ES+) m/z Calcd for $C_{21}H_{20}ClNO_3$+H [(M+H)+]: 370.1205. Found: 370.1205.

EXAMPLE 27

Preparation of Rac-(1R,2R)-6'-chloro-2-(3,5-dichlorophenyl)spiro[5-cyclohexene-1,3'-[3H]indole]-2',4(1'H)-dione, Rac-(1R,2S)-6'-chloro-2-(3,5-dichlorophenyl)spiro[5-cyclohexene-1,3'-[3H]indole]-2',4(1'H)-dione, and Rac-(1R,2S,6S)-6'-chloro-2-(3,5-dichlorophenyl)-6-methoxyspiro[cyclohexane-1,3'-[3H]indole]-2',4(1'H)-dione

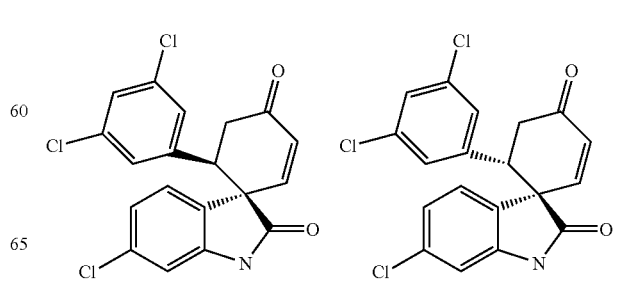

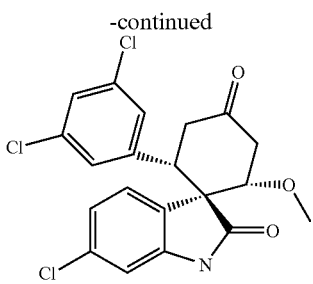

In a manner similar to the method described in example 16, E/Z-6-chloro-3-(3,5-dichlorobenzylidene)-1,3-dihydro-indol-2-one (0.32 g, 1.0 mmol) was reacted with (3-methoxy-1-methylene-allyloxy)-trimethyl-silane (0.21 g, 1.2 mmol) in toluene to give rac-(1R,2R)-6'-chloro-2-(3,5-dichlorophenyl)spiro[5-cyclohexene-1,3'-[3H]indole]-2',4(1'H)-dione (0.01 g, 2.5%) as white solid. HRMS (ES$^+$) m/z Calcd for $C_{19}H_{12}Cl_3NO_2$+H [(M+H)$^+$]: 392.007. Found: 392.006; rac-(1R,2S)-6'-chloro-2-(3,5-dichlorophenyl)spiro[5-cyclohexene-1,3'-[3H]indole]-2',4(1'H)-dione (0.091 g, 23.3%) as white solid. HRMS (ES$^+$) m/z Calcd for $C_{19}H_{12}Cl_3NO_2$+H [(M+H)$^+$]: 392.007. Found: 392.006; and rac-(1R,2S,6S)-6'-chloro-2-(3,5-dichlorophenyl)-6-methoxyspiro[cyclophexane-1,3'-[3H]indole]-2',4(1'H)-dione (0.176 g, 41.9%) as white solid. HRMS (ES$^+$) m/z Calcd for $C_{20}H_{16}Cl_3NO_3$+H [(M+H)$^+$]: 424.0269. Found: 424.0269.

EXAMPLE 28

Preparation of Rac-(1R,2R)-6'-chloro-2-(3-methylphenyl)spiro[5-cyclohexene-1,3'-[3H]indole]-2',4(1'H)-dione, Rac-(1R,2S)-6'-chloro-2-(3-methylphenyl)spiro[5-cyclohexene-1,3'-[3H]indole]-2',4(1'H)-dione, and Rac-(1R,2S,6S)-6'-chloro-2-(3methylphenyl)-6-methoxyspiro[cyclohexane-1,3'-[3H]indole]-2',4(1'H)-dione

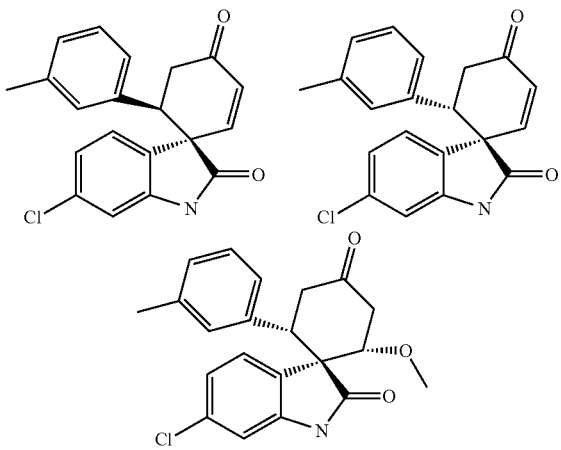

In a manner similar to the method described in example 16, E/Z-6-chloro-3-(3-methylbenzylidene)-1,3-dihydro-indol-2-one (0.27 g, 1.0 mmol) was reacted with (3-methoxy-1-methylene-allyloxy)-trimethyl-silane (0.21 g, 1.2 mmol) in toluene to give rac-(1R,2R)-6'-chloro-2-(3-methylphenyl)spiro[5-cyclohexene-1,3'-[3H]indole]-2',4(1'H)-dione (0.016 g, 4.6%) as white amorphous. HRMS (ES$^+$) m/z Calcd for $C_{20}H_{16}ClNO_2$+H [(M+H)$^+$]: 338.0943. Found: 338.0943; rac-(1R,2S)-6'-chloro-2-(3-methylphenyl)spiro[5-cyclohexene-1,3'-[3H]indole]-2',4(1'H)-dione (0.101 g, 29.8%) as white amorphous. HRMS (ES$^+$) m/z Calcd for $C_{20}H_{16}ClNO_2$+H [(M+H)$^+$]: 338.0943. Found: 338.0943; and rac-(1R,2S,6S)-6'-chloro-2-(3-methylphenyl)-6-methoxyspiro[cyclohexane-1,3'-[3H]indole]-2',4(1'H)-dione (0.117 g, 31.6%) as white amorphous. HRMS (ES$^+$) m/z Calcd for $C_{20}H_{20}ClNO_3$+H [(M+H)$^+$]: 370.1205. Found: 370.1206.

EXAMPLE 29

Preparation of Rac-(1R,2R)-6'-chloro-2-(3-pyridineyl)spiro[5-cyclohexene-1,3'-[3H]indole]-2',4(1'H)-dione, and Rac-(1R,2S)-6'-chloro-2-(3-pyridineyl)spiro[5-cyclohexene-1,3'-[3H]indole]-2',4(1'H)-dione

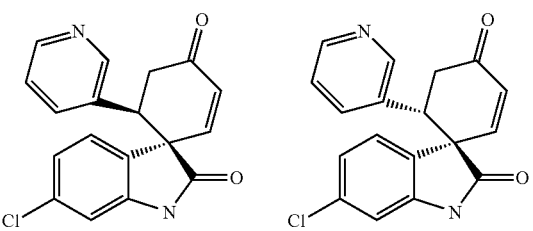

In a manner similar to the method described in example 16, E/Z-6-chloro-3-(pyridine-3-yl)-1,3-dihydro-indol-2-one (0.26 g, 1.0 mmol) was reacted with (3-methoxy-1-methylene-allyloxy)-trimethyl-silane (0.21 g, 1.2 mmol) in toluene to give rac-(1R,2R)-6'-chloro-2-(pyridine-3yl)spiro[5-cyclohexene-1,3'-[3H]indole]-2',4(1'H)-dione (0.010 g, 3.2%) as white amorphous. HRMS (ES$^+$) m/z Calcd for $C_{18}H_{13}ClN_2O_2$+H [(M+H)$^+$]: 325.0739. Found: 325.0739; rac-(1R,2S)-6'-chloro-2-(3-methylhenyl)spiro[5-cyclohexene-1,3'-[3H]indole]-2',4(1'H)-dione (0.015 g, 4.6%) as white solid. HRMS (ES$^+$) m/z Calcd for $C_{18}H_{13}ClN_2O_2$+H [(M+H)$^+$]: 325.0739. Found: 325.0738.

EXAMPLE 30

Preparation of Rac-(1R,2R)-6'-chloro-2-(thien-3-yl)spiro[5-cyclohexene-1,3'-[3H]indole]-2',4(1'H)-dione, Rac-(1R,2S)-6'-chloro-2-(thien-3-yl)spiro[5-cyclohexene-1,3'-[3H]indole]-2',4(1'H)-dione, and Rac-(1R,2S,6S)-6'-chloro-2-(thien-3-yl)-6-methoxyspiro[cyclohexane-1,3'-[3H]indole]-2',4(1'H)-dione

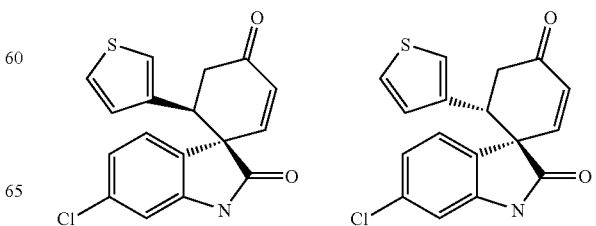

-continued

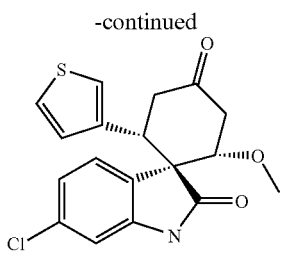

In a manner similar to the method described in example 16, E/Z-6-chloro-3-(3-methylbenzylidene)-1,3-dihydro-indol-2-one (0.26 g, 1.0 mmol) was reacted with (3-methoxy-1-methylene-allyloxy)-trimethyl-silane (0.21 g, 1.2 mmol) in toluene to give rac-(1R,2R)-6'-chloro-2-(thien-3-yl)spiro[5-cyclohexene-1,3'-[3H]indole]-2',4(1'H)-dione (0.024 g, 7.3%) as white amorphous. HRMS (ES+) m/z Calcd for $C_{17}H_{12}ClNO_2S+H$ [(M+H)+]: 330.0350. Found: 330.0351; rac-(1R,2S)-6'-chloro-2-(thien-3-yl)spiro[5-cyclohexene-1,3'-[3H]indole]-2',4(1'H)-dione (0.109 g, 32.9%) as white amorphous. HRMS (ES+) m/z Calcd for $C_{17}H_{12}ClNO_2S+H$ [(M+H)+]: 330.0350. Found: 330.0351; and rac-(1R,2S,6S)-6'-chloro-2-(thien-3-yl)-6-methoxyspiro[cyclohexane-1,3'-[3H]indole]-2',4(1'H)-dione (0.145 g, 40.3%) as white amorphous. HRMS (ES+) m/z Calcd for $C_{18}H_{16}ClNO_3S+H$ [(M+H)+]: 362.0612. Found: 362.0613.

EXAMPLE 31

Preparation of Rac-(1R,2S)-6'-chloro-2-(3-chlorophenyl)spiro[5-cyclohexene-1,3'-[3H]indole]-2',4(1'H)-dione from Rac-(1R,2S,6S)-6'-chloro-2-(3-chlorophenyl)-6-methoxyspiro[cyclohexane-1,3'-[3H]indole]-2',4(1'H)-dione (Scheme 2)

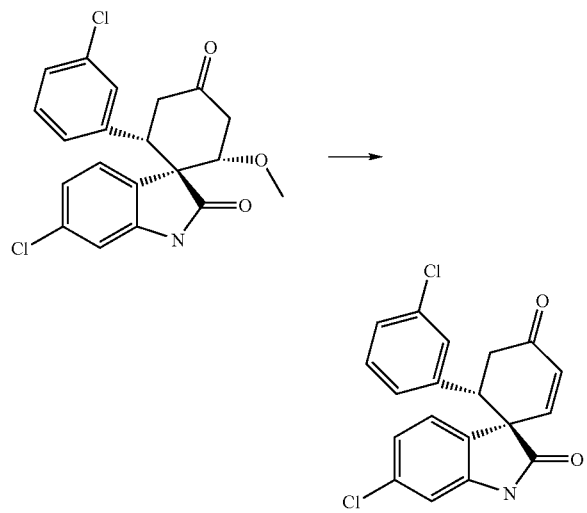

To a suspension of Rac-(1R,2S,6S)-6'-chloro-2-(3-chlorophenyl)-6-methoxyspiro[cyclohexane-1,3'-[3H]indole]-2',4(1'H)-dione (1.28 g) in toluene (10 mL) was added reagent p-TSA and the reaction mixture was allowed to stir at 120° C. for 10 min with CEM microwave (3×seared tubes). After cooled to rt, the precipitates were collected by filtration and the solid was washed with ether and dried to give Rac-(1R,2S)-6'-chloro-2-(3-chlorophenyl)spiro[5-cyclohexene-1,3'-[3H]indole]-2',4(1'H)-dione (1.18 g, 100%) as yellowish solid.

EXAMPLE 32

Preparation of Rac-(1R,2S,6R)-6'-chloro-2-(3-chlorophenyl)-6-phenylspiro[cyclohexane-1,3'-[3H]indole]-2',4(1'H)-dione (Scheme 3)

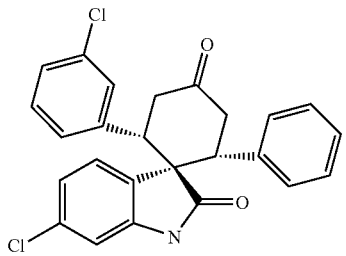

In a flask equipped with septum and stirring bar, a mixture of CuCl (17.6 mg, 0.18 mmol) and Ph$_3$P (76.1 mg, 0.21 mmol) was suspended in THF (2 mL). After stirring under argon at rt for 30 min, rac-(1R,2S)-6'-chloro-2-(3-chlorophenyl)spiro[5-cyclohexene-1,3'-[3H]indole]-2',4(1'H)-dione (100 mg, 0.28 mmol) was added in one portion. After additional stirring for 10 min, phenylmagnesium bromide (3.0 M in ether, 0.28 mL, 0.84 mmol) was added dropwise to the resulting mixture during 5 min at 0° C. After stirring under argon at 0° C. to −10° C. for 1 h, the reaction mixture was allowed to stir overnight with the ice-bath. Sat.NH4Cl was then added to the reaction mixture. The organic phase was separated. TLC/MS (AcOEt/Hex=1/2) showed mixture of two isomers of the desired products and no SM. The mixture was then separated by flash column to give Rac-(1R,2S,6R)-6'-chloro-2-(3-chlorophenyl)-6-phenylspiro[cyclohexane-1,3'-[3H]indole]-2',4(1'H)-dione (85.6 mg, 79.0%) as white solid, HRMS (ES+) m/z Calcd for $C_{25}H_{19}Cl_2NO_2+H$ [(M+H)+]: 436.0866. Found: 436.0864.

EXAMPLE 33

Preparation of Rac-(1S,2S,6R)-6'-chloro-2-(3-chlorophenyl)-6-(5-fluoro-2-methylphenyl)spiro[cyclohexane-1,3'-[3H]indole]-2',4(1'H)-dione

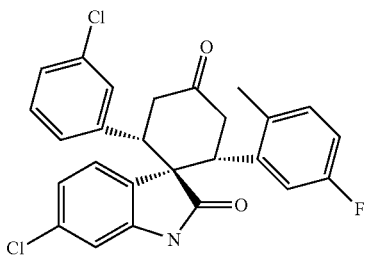

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 5-fluoro-2-methylphenylmagnesium bromide (0.5 M in THF, 0.84 mL, 0.42 mmol) in THF to give Rac-(1S,2S,6R)-6'-chloro-2-(3-chlorophenyl)-6-(5-fluoro-2-methylphenyl)spiro[cyclohexane-1,3'-[3H]indole]-2',4(1'H)-dione (24.9 mg, 37.8%) as white solid. HRMS (ES$^+$) m/z Calcd for $C_{26}H_{20}Cl_2FNO_2$+H [(M+H)$^+$]: 468.0928 Found: 468.0928.

EXAMPLE 34

Preparation of Rac-(1R,2S,6R)-6'-chloro-2-(3-chlorophenyl)-6-(3-methoxyphenyl)spiro[cyclohexane-1,3'-[3H]indole]-2',4(1'H)-dione

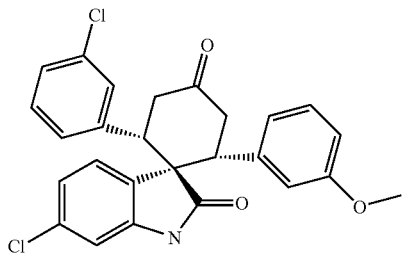

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 3-methoxylphenylmagnesium bromide (1.0 M in THF, 0.70 mL, 0.70 mmol) in THF to give Rac-(1R,2S,6R)-6'-chloro-2-(3-chlorophenyl)-6-(3-methoxyphenyl)spiro[cyclohexane-1,3'-[3H]indole]-2',4(1'H)-dione (40.4 mg, 61.9%), as white solid. HRMS (ES$^+$) m/z Calcd for $C_{26}H_{21}Cl_2NO_3$+H [(M+H)$^+$]: 466.0971. Found: 466.0971.

EXAMPLE 35

Preparation of Rac-(1R,2S,6R)-6'-chloro-2-(3-chlorophenyl)-6-(3-fluorophenyl)spiro[cyclohexane-1,3'-[3H]indole]-2',4(1'H)-dione

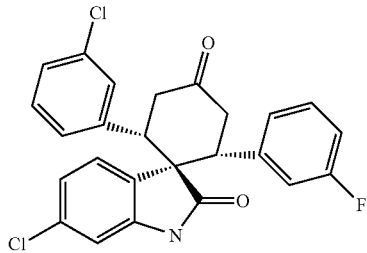

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 3-fluorophenylmagnesium bromide (1.0 M in THF, 0.70 mL, 0.70 mmol) in THF to give Rac-(1R,2S,6R)-6'-chloro-2-(3-chlorophenyl)-6-(3-fluorophenyl)spiro[cyclohexane-1,3'-[3H]indole]-2',4(1'H)-dione (41.6 mg, 65.5%), as white solid. HRMS (ES$^+$) m/z Calcd for $C_{25}H_{18}Cl_2FNO_2$+H [(M+H)$^+$]: 454.0772. Found: 454.0773.

EXAMPLE 36

Preparation of Rac-(1S,2S,6R)-6'-chloro-2-(3-chlorophenyl)-6-(2-methylphenyl)spiro[cyclohexane-1,3'-[3H]indole]-2',4(1'H)-dione

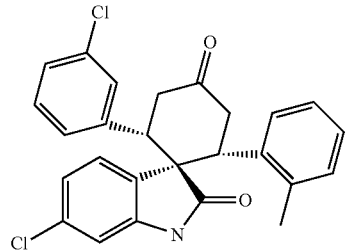

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 2-methylphenylmagnesium bromide (2.0 M in ether, 0.35 mL, 0.70 mmol) in THF to give Rac-(1S,2S,6R)-6'-chloro-2-(3-chlorophenyl)-6-(2-methylphenyl)spiro[cyclohexane-1,3'-[3H]indole]-2',4(1'H)-dione (28.6 mg, 45.3%), as white amorphous. HRMS (ES$^+$) m/z Calcd for $C_{26}H_{21}Cl_2NO_2$+H [(M+H)$^+$]: 450.1022. Found: 450.1021.

EXAMPLE 37

Preparation of Rac-(1S,2S,6R)-6'-chloro-2-(3-chlorophenyl)-6-(3-chloro-5-fluorophenyl)spiro[cyclohexane-1,3'-[3H]indole]-2',4(1'H)-dione

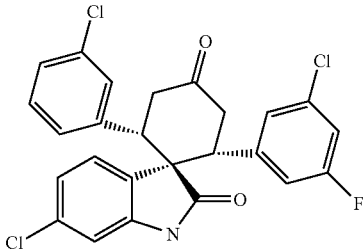

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 3-chloro-5-fluorophenylmagnesium bromide (0.5 M in THF, 1.40 mL, 0.70 mmol) in THF to give Rac-(1S,2S,6R)-6'-chloro-2-(3-chlorophenyl)-6-(3-chloro-5-fluorophenyl)spiro[cyclohexane-1,3'-[3H]indole]-2',4(1'H)-dione (45.6 mg, 66.6%), as white amorphous. HRMS (ES$^+$) m/z Calcd for $C_{25}H_{17}Cl_3FNO_2$+H [(M+H)$^+$]: 488.0382. Found: 488.0380.

EXAMPLE 38

Preparation of Meso-6'-chloro-2-(3-chlorophenyl)-6-(3-chlorophenyl)spiro[cyclohexane-1,3'-[3H]indole]-2',4(1'H)-dione

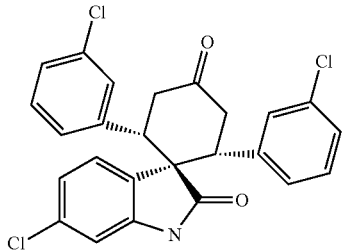

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 3-chlorophenylmagnesium bromide (0.5 M in THF, 1.40 mL, 0.70 mmol) in THF to give Meso-6'-chloro-2-(3-chlorophenyl)-6-(3-chlorophenyl)spiro[cyclohexane-1, 3'-[3H]indole]-2',4(1'H)-dione (46.2 mg, 70.1%), as white amorphous. HRMS (ES+) m/z Calcd for $C_{25}H_{18}Cl_3NO_2$+H [(M+H)+]: 470.0476. Found: 470.0476.

EXAMPLE 39

Preparation of Rac-(1R,2S,6R)-6'-chloro-2-(3-chlorophenyl)-6-(3-methylphenyl)spiro[cyclohexane-1,3'-[3H]-indole]-2',4(1'H)-dione

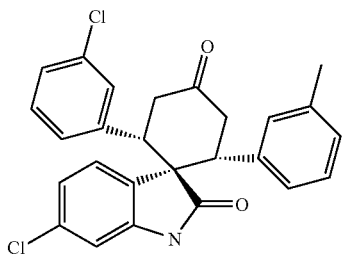

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 3-methylphenylmagnesium bromide (1.0 M in THF, 0.70 mL, 0.70 mmol) in THF to give Rac-(1R,2S, 6R)-6'-chloro-2-(3-chlorophenyl)-6-(3-methylphenyl)spiro [cyclohexane-1,3'-[3H]indole]-2',4(1'H)-dione (43.8 mg, 69.4%), as white amorphous. HRMS (ES+) m/z Calcd for $C_{26}H_{21}Cl_2NO_2$+H [(M+H)+]: 450.1022. Found: 450.1019.

EXAMPLE 40

Preparation of Rac-(1S,2S,6R)-6'-chloro-2-(3-chlorophenyl)-6-(3-thionyl)spiro[cyclohexane-1,3'-[3H]indole]-2',4(1'H)-dione

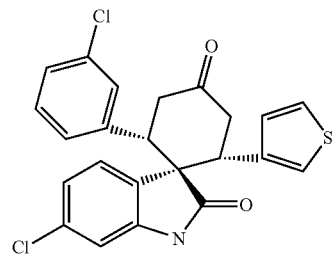

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 3-thienylmagnesium iodide (0.3 M in THF, 2.33 mL, 0.70 mmol) in THF to give Rac-(1S,2S,6R)-6'-chloro-2-(3-chlorophenyl)-6-(thien-3-yl)spiro[cyclohexane-1,3'-[3H]indole]-2',4(1'H)-dione (8.6 mg, 13.9%), as white solid. HRMS (ES+) m/z Calcd for $C_{23}H_{17}Cl_2NO_2S$+H [(M+H)+]: 442.0430. Found: 442.0429.

EXAMPLE 41

Preparation of Rac-(1R,2S,6S)-6'-chloro-2-(3-chlorophenyl)-6-ethylspiro[cyclohexane-1,3'-[3H]indole]-2',4(1'H)-dione and Rac-(1R,2S,6R)-6'-chloro-2-(3-chlorophenyl)-6-ethylspiro[cyclohexane-1,3'-[3H]indole]-2',4(1'H)-dione

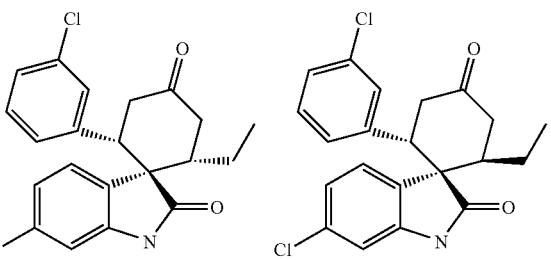

In a manner similar to the method described in example xx, rac-(1R,2S)-6'-chloro-2-(3-chlorophenyl)spiro[5-cyclohexene-1,3'-[3H]indole]-2',4(1'H)-dione (100 mg, 0.28 mmol) was reacted with ethylmagnesium bromide (1.0 M in THF, 0.3 mL, 0.30 mmol) in THF to give Rac-(1R,2S,6S)-6'-chloro-2-(3-chlorophenyl)-6-ethylspiro[cyclohexane-1,3'-[3H]indole]-2',4(1'H)-dione (8.2 mg, 7.6%) as white amorphous. HRMS (ES+) m/z Calcd for $C_{21}H_{19}Cl_2NO_2$+H [(M+H)+]: 388.0866.

Found: 388.0866 and Rac-(1R,2S,6R)-6'-chloro-2-(3-chlorophenyl)-6-ethylspiro[cyclohexane-1,3'-[3H]indole]-2',4(1'H)-dione (11.4 mg, 10.5%) as white amorphous. HRMS (ES+) m/z Calcd for $C_{21}H_{19}Cl_2NO_2$+H [(M+H)+]: 388.0866. Found: 388.0865.

EXAMPLE 42

Preparation of Rac-(1R,2S,6R)-6'-chloro-2-(3-chlorophenyl)-6-vinylspiro[cyclohexane-1,3'-[3H]indole]-2',4(1'H)-dione and Rac-(1R,2S,6S)-6'-chloro-2-(3-chlorophenyl)-6-vinylspiro[cyclohexane-1,3'-[3H]indole]-2',4(1'H)-dione

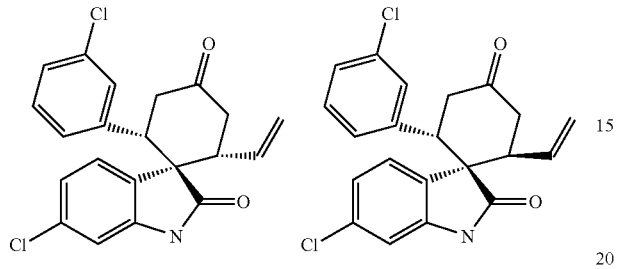

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with vinylmagnesium bromide (1.0 M in THF, 0.70 mL, 0.70 mmol) in THF to give Rac-(1R,2S,6R)-6'-chloro-2-(3-chlorophenyl)-6-vinylspiro[cyclohexane-1,3'-[3H]indole]-2',4(1'H)-dione (9.8 mg, 18.1%) as white amorphous. HRMS (ES$^+$) m/z Calcd for $C_{21}H_{17}Cl_2NO_2$+H [(M+H)$^+$]: 386.0709. Found: 386.0712: and Rac-(1R,2S,6S)-6'-chloro-2-(3-chlorophenyl)-6-vinylspiro[cyclohexane-1,3'-[3H]indole]-2',4(1'H)-dione (14.5 mg, 26.9%) as wite amorphous. HRMS (ES$^+$) m/z Calcd for $C_{21}H_{17}Cl_2NO_2$+H [(M+H)$^+$]: 386.0709. Found: 386.0707.

EXAMPLE 43

Preparation of Rac-(1R,2S,6R)-6'-chloro-2-(3-chlorophenyl)-6-isopropylspiro[cyclohexane-1,3'-[3H]indole]-2',4(1'H)-dione and Rac-(1R,2S,6S)-6'-chloro-2-(3-chlorophenyl)-6-isopropylspiro[cyclohexane-1,3'-[3H]indole]-2',4(1'H)-dione

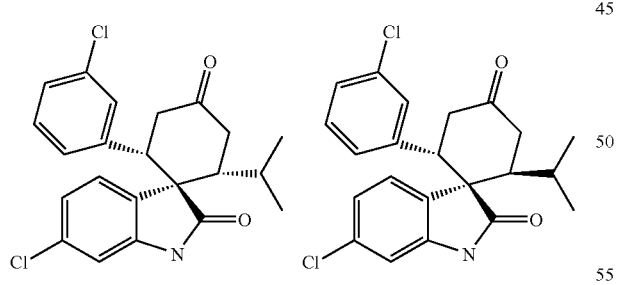

In a manner similar to the method described in example xx, rac-(1R,2S)-6'-chloro-2-(3-chlorophenyl)spiro[5-cyclohexene-1,3'-[3H]indole]-2',4(1'H)-dione (100 mg, 0.28 mmol) was reacted with isopropylmagnesium bromide (1.0 M in THF, 0.56 mL, 0.56 mmol) in THF to give Rac-(1R,2S,6R)-6'-chloro-2-(3-chlorophenyl)-6-isopropylspiro[cyclohexane-1,3'-[3H]indole]-2',4(1'H)-dione (18.3 mg, 16.9%) as white amorphous. HRMS (ES$^+$) m/z Calcd for $C_{22}H_{21}Cl_2NO_2$+H [(M+H)$^+$]: 402.1022. Found: 402.1021, and Rac-(1R,2S,6S)-6'-chloro-2-(3-chlorophenyl)-6-isopropylspiro[cyclohexane-1,3'-[3H]indole]-2',4(1'H)-dione (15.6 mg, 14.4%) as white amorpehous. HRMS (ES$^+$) m/z Calcd for $C_{22}H_{21}Cl_2NO_2$+H [(M+H)$^+$]: 402.1022. Found: 402.1021.

EXAMPLE 44

Preparation of Rac-(1R,2S,6R)-6'-chloro-2-(3-chlorophenyl)-6-(1-methylpropyl)spiro[cyclohexane-1,3'-[3H]indole]-2',4(1'H)-dione

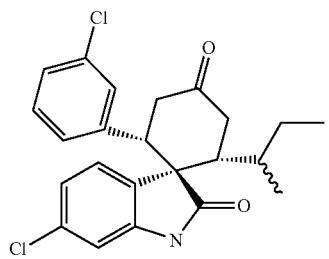

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with sec-butylmagnesium bromide (16% in THF, 0.70 mL, 0.70 mmol) in THF to give Rac-(1R,2S,6R)-6'-chloro-2-(3-chlorophenyl)-6-(1-methylpropyl)spiro[cyclohexane-1,3'-[3H]indole]-2',4(1'H)-dione (15.6 mg, 31.2%) as a diastereoitsoiers mixture as white amorphous HRMS (ES$^+$) m/z Calcd for $C_{23}H_{23}Cl_2NO_2$+H [(M+H)$^+$]: 416.1179. Found: 416.1179.

EXAMPLE 45

Preparation of Rac-(1R,2S,6R)-6'-chloro-2-(3-chlorophenyl)-6-(1-methyl-propenyl)spiro[cyclohexane-1,3'-[3H]indole]-2',4(1'H)-dione

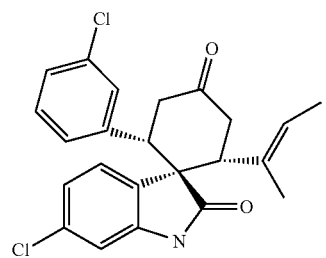

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 1-methyl-propenylmagnesium bromide (0.5 M in THF, 1.40 mL, 0.70 mmol) in THF to give Rac-(1R,2S,6R)-6'-chloro-2-(3-chlorophenyl)-6-(1-methyl-propenyl)spiro[cyclohexane-1,3'-[3H]indole]-2',4(1'H)-dione (15.2 mg, 30.0%) as a single isomer as white amorphous. HRMS (ES$^+$) m/z Calcd for $C_{23}H_{21}Cl_2NO_2$+H [(M+H)$^+$]: 414.1022. Found: 414.1022.

EXAMPLE 46

Preparation of Rac-(1R,2S,6R)-6'-chloro-2-(3-chlorophenyl)-6-iso-propenylspiro[cyclohexane-1,3'-[3H]indole]-2',4(1'H)-dione

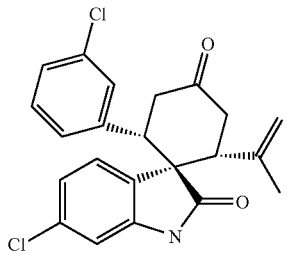

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with iso-propenylmagnesium bromide (0.5 M in THF, 1.40 mL, 0.70 mmol) in THF to give Rac-(1R,2S,6R)-6'-chloro-2-(3-chlorophenyl)-6-iso-propenylspiro[cyclohexane-1,3'-[3H]indole]-2',4(1'H)-dione (28.6 mg, 56.4%) as a single isomer as white amorphous. HRMS (ES$^+$) m/z Calcd for $C_{22}H_{19}Cl_2NO_2$+H [(M+H)$^+$]: 400.0866. Found: 400.0866.

EXAMPLE 47

Preparation of Rac-(1S,2S,6R)-6'-chloro-2-(3-chlorophenyl)-6-(1,1-dimethyl-propyl)spiro[cyclohexane-1,3'-[3H]indole]-2',4(1'H)-dione

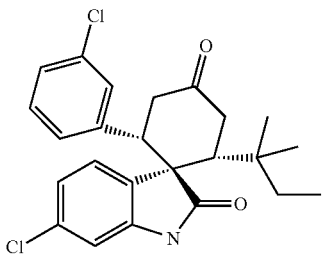

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with 1,1-dimethylpropylmagnesium chloride (1.0 M in THF, 0.70 mL, 0.70 mmol) in THF to give Rac-(1S,2S,6R)-6'-chloro-2-(3-chlorophenyl)-6-(1,1-dimethyl-propyl)spiro[cyclohexane-1,3'-[3H]indole]-2',4(1'H)-dione (18.2 mg, 30.3%) as a single isomer as white amorphous. HRMS (ES$^+$) m/z Calcd for $C_{24}H_{25}Cl_2NO_2$+H [(M+H)$^+$]: 430.1335. Found: 430.1333.

EXAMPLE 48

Preparation of Rac-(1S,2S,6R)-6'-chloro-2-(3-chlorophenyl)-6-(tert-butyl)spiro[cyclohexane-1,3'-[3H]indole]-2',4(1'H)-dione

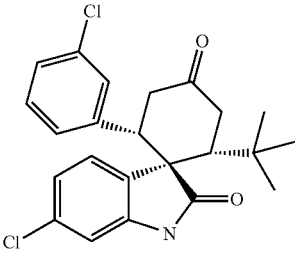

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with tert-butylpropylmagnesium chloride (1.0 M in THF, 0.70 mL, 0.70 mmol) in THF to give Rac-(1S,2S,6R)-6'-chloro-2-(3-chlorophenyl)-6-(1,1-dimethyl-propyl)spiro[cyclohexane-1,3'-[3H]indole]-2',4(1'H)-dione (15.5 mg, 26.6%) as a single isomer as whIte amorphous. HRMS (ES$^+$) m/z Calcd for $C_{23}H_{23}Cl_2NO_2$H [(M+H)$^+$]: 416.1179. Found: 416.1178.

EXAMPLE 49

Preparation of Rac-(1R,2S,6R)-6'-chloro-2-(3-chlorophenyl)-6-cyclopentylspiro[cyclohexane-1,3'-[3H]indole]-2',4(1'H)-dione and Rac-(1R,2S,6S)-6'-chloro-2-(3-chlorophenyl)-6-cyclopentylspiro[cyclohexane-1,3'-[3H]indole]-2',4(1'H)-dione

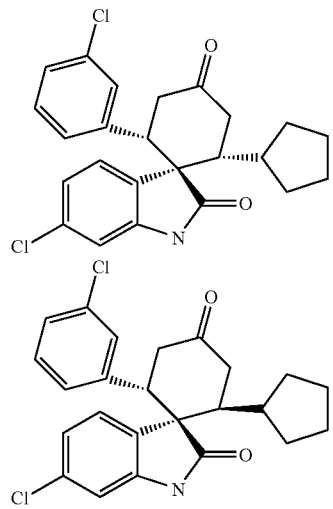

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with cyclopentylmagnesium bromide (2.0 M in ether, 0.35 mL, 0.70 mmol) in THF to give Rac-(1R,2S,6R)-6'-chloro-2-(3-chlorophenyl)-6-cyclopentylspiro[cyclohexane-1,3'-[3H]indole]-2',4(1'H)-dione (19.6 mg, 32.7%) as white solid. HRMS (ES$^+$) m/z Calcd for $C_{24}H_{23}Cl_2NO_2$+H [(M+H)$^+$]: 428.1179 Found: 428.1180, and Rac-(1R,2S,6)-6'-chloro-2-(3-chlorophenyl)-6-cyclopentylspiro[cyclohexane-1,3'-[3H]indole]-2',4(1'H)-dione (6.2 mg, 10.3%) as white amorphous. HRMS (ES+) m/z Calcd for $C_{24}H_{23}Cl_2NO_2$+H [(M+H)+]: 428.1179. Found: 428.1178.

EXAMPLE 50

Preparation of Rac-(1R,2S,6R)-6'-chloro-2-(3-chlorophenyl)-6-cyclopropylspiro[cyclohexane-1,3'-[3H]indole]-2',4(1'H)-dione and Rac-(1R,2S,6S)-6'-chloro-2-(3-chlorophenyl)-6-cyclopropylspiro[cyclohexane-1,3'-[3H]indole]-2',4(1'H)-dione

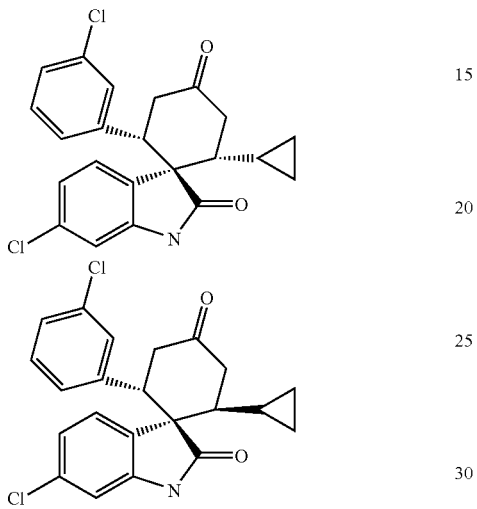

In a manner similar to the method described in example xx, rac-(1R,2S)-6'-chloro-2-(3-chlorophenyl)spiro[5-cyclohexene-1,3'-[3H]indole]-2',4(1'H)-dione (50 mg, 0.14 mmol) was reacted with cyclopropylmagnesium bromide (0.5 M in THF, 1.4 mL, 0.70 mmol) in THF to give Rac-(1S,2S,6S)-6'-chloro-2-(3-chlorophenyl)-6-cyclopropylspiro[cyclohexane-1,3'-[3H]indole]-2',4(1'H)-dione (19.8 mg, 35.4%) as white solid. HRMS (ES+) m/z Calcd for $C_{22}H_{19}Cl_2NO_2$+H [(M+H)+]: 400.0866. Found: 400.0865, and Rac-(1S,2S,6R)-6'-chloro-2-(3-chlorophenyl)-6-cyclopropylspiro[cyclohexane-1,3'-[3H]indole]-2',4(1'H)-dione (17.1 mg, 30.5%) as white solid. HRMS (ES+) m/z Calcd for $C_{22}H_{19}Cl_2NO_2$+H [(M+H)+]: 400.0866. Found: 400.0866.

EXAMPLE 51

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$'s showing the biological activity of this invention exhibit activities less than about 10 µM.

What is claimed:

1. A compound of the formula

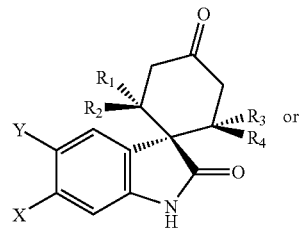

Ia

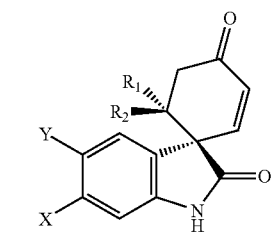

Ib wherein

X is selected from the group consisting of hydrogen, halogen, cyano, nitro, ethynyl, cyclopropyl, Y is hydrogen, $R_1$, $R_2$, $R_3$ and $R_4$ are selected from the group consisting of hydrogen, lower alkyl and lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_2$ or $R_3/R_4$ is hydrogen and the other not hydrogen, and the pharmaceutically acceptable salts and esters thereof.

2. A compound of the formula

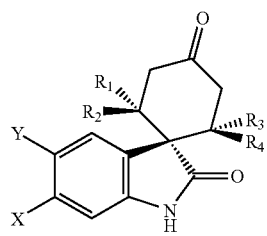

Ia

I wherein

X is halogen,
Y is hydrogen,
$R_2$ is hydrogen,
$R_4$ is hydrogen and
$R_1$, and $R_3$ are selected from the group consisting of hydrogen, lower alkyl and lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_3$ is a meta-halogen substituted phenyl with or without further substitution and the pharmaceutically acceptable salts and esters thereof.

3. The compound of claim 2 wherein
X is fluorine, chlorine or bromine,
Y is hydrogen,
$R_2$ is hydrogen,
$R_4$ is hydrogen and
one of $R_1/R_3$ is a meta-halogen substituted phenyl with or without further substitution and the other of $R1/R_3$ is selected from the group consisting of lower alkyl and substituted lower alkyl, lower alkenyl, substituted lower alkenyl, aryl, substituted aryl.

4. A compound of claim 1 selected from the group consisting of

Rac-(1R,2S,6S)-6'-chloro-2-(3-chlorophenyl)-6-methoxyspiro[cyclohexane-1,3'-[3H]indole]-2',4(1'H)-dione, Rac-(1R,2S,6S)-6'-chloro-2-(4-chlorophenyl)-6-methoxyspiro[cyclohexane-1,3'-[3H]indole]-2',4(1'H)-dione, Rac-(1R,2S,6S)-6'-chloro-2-(3-chloro-2-fluorophenyl)-6-methoxyspiro[cyclohexane-1,3'-[3H]indole]-2',4(1'H)-dione, Rac-(1R,2S,6S)-6'-chloro-2-(3-cyanophenyl)-6-methoxyspiro[cyclohexane-1,3'-[3H]indole]-2',4(1'H)-dione, Rac-(1R,2S,6S)-6'-chloro-2-(3-bromophenyl)-6-methoxyspiro[cyclohexane-1,3'-[3H]indole]-2',4(1'H)-dione, Rac-(1R,2S,6S)-6'-chloro-2-(2-methylphenyl)-6-methoxyspiro[cyclohexane-1,3'-[3H]indole]-2',4(1'H)-dione, Rac-(1R,2S,6S)-6'-chloro-2-(3,5-dichlorophenyl)-6-methoxyspiro[cyclohexane-1,3'-[3H]indole]-2',4(1'H)-dione, Rac-(1R,2S,6S)-6'-chloro-2-(3-methylphenyl)-6-methoxyspiro[cyclohexane-1,3'-[3H]indole]-2',4(1'H)-dione, ac-(1R,2R,6S)-6'-chloro-2-(3-thienyl)-6-methoxyspiro[cyclohexane-1,3'-[3H]indole]-2',4(1'H)-dione and Rac-(1R,2S,6R)-6'-chloro-2-(3-chlorophenyl)-6-phenylspiro[cyclohexane-1,3'-[3H]indole]-2',4(1'H)-dione.

5. A compound of claim 1 selected from the group consisting of

Rac-(1S,2S,6R)-6'-chloro-2-(3-chlorophenyl)-6-(5-fluoro-2-methylphenyl)spiro[cyclohexane-1,3'-[3H]indole]-2',4(1'H)-dione, Rac-(1R,2S,6R)-6'-chloro-2-(3-chlorophenyl)-6-(3-methoxylphenyl)spiro[cyclohexane-1,3'-[3H]indole]-2',4(1'H)-dione, Rac-(1R,2S,6R)-6'-chloro-2-(3-chlorophenyl)-6-(3-fluorophenyl)spiro[cyclohexane-1,3'-[3H]indole]-2',4(1'H)-dione, Rac-(1S,2S,6R)-6'-chloro-2-(3-chlorophenyl)-6-(2-methylphenyl)spiro[cyclohexane-1,3'-[3H]indole]-2',4(1'H)-dione, Rac-(1S,2S,6R)-6'-chloro-2-(3-chlorophenyl)-6-(3-chloro-5-fluorophenyl)spiro[cyclohexane-1,3'-[3H]indole]-2',4(1'H)-dione, Meso-6'-chloro-2-(3-chlorophenyl)-6-(3-chlorophenyl)spiro[cyclohexane-1,3'-[3H]indole]-2',4(1'H)-dione, Rac-(1R,2S,6R)-6'-chloro-2-(3-chlorophenyl)-6-(3-methylphenyl)spiro[cyclohexane-1,3'-[3H]indole]-2',4(1'H)-dione, Rac-(1S,2S,6R)-6'-chloro-2-(3-chlorophenyl)-6-(3-thionyl)spiro[cyclohexane-1,3'-[3H]indole]-2',4(1'H)-dione, Rac-(1R,2S,6S)-6'-chloro-2-(3-chlorophenyl)-6-ethylspiro[cyclohexane-1,3'-[3H]indole]-2',4(1'H)-dione, Rac-(1R,2S,6R)-6'-chloro-2-(3-chlorophenyl)-6-ethylspiro[cyclohexane-1,3'-[3H]indole]-2',4(1'H)-dione and Rac-(1R,2S,6R)-6'-chloro-2-(3-chlorophenyl)-6-vinylspiro[cyclohexane-1,3'-[3H]indole]-2',4(1'H)-dione.

6. A compound of claim 1 selected from the group consisting of

Rac-(1R,2S,6S)-6'-chloro-2-(3-chlorophenyl)-6-vinylspiro[cyclohexane-1,3'-[3H]indole]-2',4(1'H)-dione, Rac-(1R,2S,6R)-6'-chloro-2-(3-chlorophenyl)-6-isopropylspiro[cyclohexane-1,3'-[3H]indole]-2',4(1'H)-dione, Rac-(1R,2S,6S)-6'-chloro-2-(3-chlorophenyl)-6-isopropylspiro[cyclohexane-1,3'-[3H]indole]-2',4(1'H)-dione, Rac-(1R,2S,6R)-6'-chloro-2-(3-chlorophenyl)-6-(1-methylpropyl)-spiro[cyclohexane-1,3'-[3H]indole]-2',4(1'H)-dione, Rac-(1R,2S,6R)-6'-chloro-2-(3-chlorophenyl)-6-(1-methyl-propenyl)spiro[cyclohexane-1,3'-[3H]indole]-2',4(1'H)-dione, Rac-(1R,2S,6R)-6'-chloro-2-(3-chlorophenyl)-6-iso-propenylspiro[cyclohexane-1,3'-[3H]indole]-2',4(1'H)-dione, Rac-(1S,2S,6R)-6'-chloro-2-(3-chlorophenyl)-6-(1,1-dimethyl-propyl)spiro[cyclohexane-1,3'-[3H]indole]-2',4(1'H)-dione, Rac-(1S,2S,6R)-6'-chloro-2-(3-chlorophenyl)-6-(tert-butyl)spiro[cyclohexane-1,3'-[3H]indole]-2',4(1'H)-dione, Rac-(1R,2S,6R)-6'-chloro-2-(3-chlorophenyl)-6-cyclopentylspiro[cyclohexane-1,3'-[3H]indole]-2',4(1'H)-dione, Rac-(1R,2S,6S)-6'-chloro-2-(3-chlorophenyl)-6-cyclopentylspiro[cyclohexane-1,3'-[3H]indole]-2',4(1'H)-dione, Rac-(1R,2S,6R)-6'-chloro-2-(3-chlorophenyl)-6-cyclopropylspiro[cyclohexane-1,3'-[3H]indole]-2',4(1'H)-dione and Rac-(1R,2S,6S)-6'-chloro-2-(3-chlorophenyl)-6-cyclopropylspiro[cyclohexane-1,3'-[3H]indole]-2',4(1'H)-dione.

7. A pharmaceutical formulation comprising a compound of the

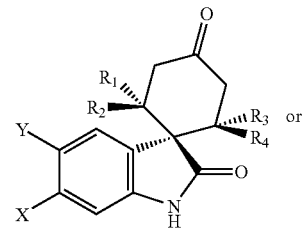

Ia

-continued

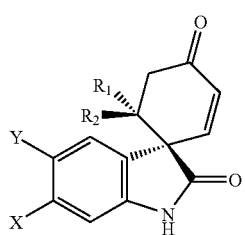

Ib wherein
X is selected from the group consisting of hydrogen, halogen, cyano, nitro, ethynyl, cyclopropyl, Y is hydrogen, $R_1$, $R_2$, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_2$ or $R_3/R_4$ is hydrogen and the other not hydrogen and the pharmaceutically acceptable salts and esters thereof together with a pharmaceutically acceptable excipient.

* * * * *

UNITED STATES PATENT AND TRADEMARK OFFICE
CERTIFICATE OF CORRECTION

PATENT NO. : 7,638,548 B2  Page 1 of 1
APPLICATION NO. : 11/867155
DATED : December 29, 2009
INVENTOR(S) : Jin-Jun Liu and Zhuming Zhang It is certified that error appears in the above-identified patent and that said Letters Patent is hereby corrected as shown below:

In Claim 2, Column 38, Line 55, please delete " 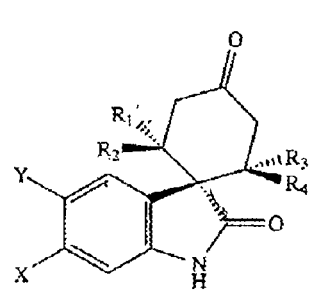 "

and insert -- 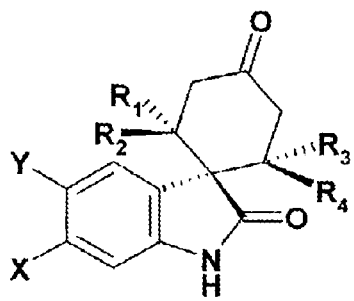 --

Signed and Sealed this
Twelfth Day of April, 2011

David J. Kappos
*Director of the United States Patent and Trademark Office*